US012390227B2

(12) United States Patent
Herregodts

(10) Patent No.: US 12,390,227 B2
(45) Date of Patent: Aug. 19, 2025

(54) BONE CUTTER AND SOFT TISSUE PROTECTOR

(71) Applicant: UNIVERSITEIT GENT, Ghent (BE)

(72) Inventor: Stijn Herregodts, Geraardsbergen (BE)

(73) Assignee: UNIVERSITEIT GENT, Ghent (BE)

( * ) Notice: Subject to any disclaimer, the term of this patent is extended or adjusted under 35 U.S.C. 154(b) by 934 days.

(21) Appl. No.: 17/261,783

(22) PCT Filed: Jul. 23, 2019

(86) PCT No.: PCT/EP2019/069819
§ 371 (c)(1),
(2) Date: Jan. 20, 2021

(87) PCT Pub. No.: WO2020/020898
PCT Pub. Date: Jan. 30, 2020

(65) Prior Publication Data
US 2021/0315591 A1 Oct. 14, 2021

(30) Foreign Application Priority Data

Jul. 23, 2018 (EP) .................................... 18184881

(51) Int. Cl.
*A61B 17/16* (2006.01)
*A61B 34/20* (2016.01)
(Continued)

(52) U.S. Cl.
CPC .............. *A61B 17/16* (2013.01); *A61B 34/20* (2016.02); *A61B 34/30* (2016.02); *A61B 2017/1602* (2013.01); *A61B 2090/065* (2016.02)

(58) Field of Classification Search
CPC . A61B 17/16; A61B 17/1615; A61B 17/1657; A61B 17/1675; A61B 2017/1602; A61B 34/20; A61B 34/25; A61B 34/30
See application file for complete search history.

(56) References Cited

U.S. PATENT DOCUMENTS 5,609,603 A 3/1997 Linden
6,001,115 A * 12/1999 Ahola .................. A61B 17/144
606/176
(Continued)

FOREIGN PATENT DOCUMENTS

CN 101516272 A 8/2009
FR 670230 A 11/1929
(Continued)

OTHER PUBLICATIONS

Extended European Search Report and Written Opinion from corresponding European Application No. 18184881.3, Jan. 18, 2019.
(Continued)

*Primary Examiner* — Si Ming Ku
(74) *Attorney, Agent, or Firm* — Workman Nydegger

(57) ABSTRACT

A bone cutting system includes an elongated surgical bone cutting tool having a first extremity for fixing the bone cutting tool to a cutting robot or machinery and a second extremity opposite thereto at the end of the elongated surgical bone cutting tool. The protection system comprises a protection element attachable to the elongated bone cutting tool. The protection element includes an interposing portion covering, when the protection element is attached to the elongated cutting tool, at least the second extremity of the elongated cutting tool, so that the interposing portion is being interposed between the soft tissue and the bone cutting tool during cutting with the elongated cutting tool, for preventing the bone cutting tool from cutting into the soft tissue. During cutting with the bone cutting tool, the protection element follows in congruence with the bone cutting tool.

20 Claims, 12 Drawing Sheets

(51) Int. Cl.
*A61B 34/30* (2016.01)
*A61B 90/00* (2016.01)

(56) References Cited

U.S. PATENT DOCUMENTS

| | | | |
|---|---|---|---|
| 9,603,610 | B2 | 3/2017 | Richter et al. |
| 10,582,943 | B2 | 3/2020 | Richter et al. |
| 11,103,316 | B2 | 8/2021 | Kostrzewski et al. |
| 11,317,925 | B2 | 5/2022 | Kuroda et al. |
| 2005/0143745 | A1 | 6/2005 | Hodorek et al. |
| 2007/0287933 | A1* | 12/2007 | Phan ............... A61B 17/320016 600/564 |
| 2011/0245833 | A1* | 10/2011 | Anderson .......... A61B 17/1628 606/80 |
| 2013/0289732 | A1 | 10/2013 | Kurtz |
| 2014/0276840 | A1 | 9/2014 | Richter et al. |
| 2016/0151120 | A1 | 6/2016 | Kostrzewski et al. |
| 2016/0192948 | A1 | 7/2016 | Wu et al. |
| 2017/0007272 | A1 | 1/2017 | Weitzman et al. |
| 2017/0196582 | A1 | 7/2017 | Richter et al. |
| 2019/0150945 | A1 | 5/2019 | Kuroda et al. |
| 2019/0175272 | A1* | 6/2019 | Khan .................. A61B 18/203 |
| 2020/0275946 | A1 | 9/2020 | Richter et al. |
| 2021/0353374 | A1 | 11/2021 | Kostrzewski et al. |

FOREIGN PATENT DOCUMENTS

| | | |
|---|---|---|
| JP | 108215202 A | 8/1996 |
| JP | 2016511074 A | 4/2016 |
| JP | 2017536909 A | 12/2017 |
| WO | 2017139674 A1 | 8/2017 |
| WO | 2018020581 A1 | 2/2018 |

OTHER PUBLICATIONS

International Search Report and Written Opinion from PCT Application No. PCT/EP2019/069819, Oct. 31, 2019.
Office Action from corresponding Japanese Patent Application No. 2021-502993, Jun. 17, 2022.
Office Action from corresponding Chinese Application No. 201980049067.5, May 24, 2023.

* cited by examiner

BONE CUTTER AND SOFT TISSUE PROTECTOR

FIELD OF THE INVENTION

The invention relates to the field of surgical instruments. More specifically it relates to an instrument for a bone cutter, for providing protection of soft tissue, and to bone cutters including such instrument.

BACKGROUND OF THE INVENTION

Bone cutting is a usual need in many surgical interventions. For example, replacing bones or parts of a bone by implants is a relatively usual intervention. It is estimated that each year, more than a million interventions relate to knees and knee replacements alone. However, the satisfaction is variable; while around 90% of interventions last 10 to 15 years, many complications arise in others, for example aseptic loosening, instability, infection, polyethylene wear, arthrofibrosis and malalignment. Many of these problems could be alleviated by providing a good quality cutting, accurate cutting planes, and reduced invasiveness by minimizing the damage to all maintained structures.

In case of replacement of parts of a bone, the main issues relating to these types of intervention are related to, on one hand, the identification of the area to be replaced, and on the other hand, to the actual intervention and removal of the region as planned. For the particular cases of a joint with damaged cartilage, the parts of bones in the joint with the damage (which need to be removed) should be correctly identified. Scanning, such as radiographic imaging, can help during the surgical planning (pre- or intraoperative) to identify the regions that need to be cut and replaced by an implant. Also, during the intervention, the cutting should not remove more or less than the region that need to be removed, so the accuracy of the cutting is important.

In particular, some areas of the bone include tendons, ligaments and soft tissue in general which are very close to the bone. Tendons and ligaments anchor to the bone in specific regions of the bone, but extend over the bone and can be partially attached to it. These ligaments and muscles may be damaged during cutting even if cutting far away from the anchoring spots of the ligaments and tendons to the bone. The risk is especially high in areas with irregular shape of the bone and limited accessibility during the intervention, such as the posterior intercondylar area. Damaging of soft tissue creates further complications, prolongs recovery and in some cases full recovery of the original motion is not possible, overall reducing quality of life of the person.

SUMMARY OF THE INVENTION

It is an object of embodiments of the present invention to provide a protection to ligaments for a bone cutter, and a system for bone cutting including such protection, which effectively reduces damage of soft tissue surrounding the bone during surgical intervention.

The present invention relates to a bone cutting system for cutting a bone of a subject, the bone cutting system comprising an elongated surgical bone cutting tool, the elongated surgical bone cutting tool having a first extremity for fixing the bone cutting tool to a cutting robot or machinery and a second extremity opposite thereto, the bone cutting system further comprising a protection system, the protection system comprising a protection element attachable to the elongated bone cutting tool and including an interposing portion covering, when the protection element is attached to the elongated bone cutting tool or its frame, at least the second extremity of the elongated cutting tool, so that the interposing portion is being interposed between the soft tissue and the bone cutting tool during cutting with the elongated cutting tool, for preventing the bone cutting tool from cutting into the soft tissue, and wherein during cutting with the bone cutting tool, the protection element follows in congruence with the bone cutting tool. The bone cutting system comprises at least one sensor for extracting a contact force of the protection element on the bone.

The at least one sensor may be included in any part of the bone cutting system, such as for instance, but not limited thereto in a part of the elongated bone cutting tool, in a part of the protection system or in a part of the frame or robot where the bone cutting tool and/or protection system may be attached to.

The at least one sensor may be a sensor for directly or indirectly sensing a contact force of the protection element on the bone.

Sensing may for instance be done by a force sensor or any suitable sensor from which a force can be derived, such as for instance a pressure sensor.

The at least one sensor may be a sensor or a combination of sensors for sensing a combined force including the contact force of the protection element on the bone, for instance a sensor for combined measuring a cutting force of the elongated cutting tool and a force of the protection element, e.g. a force of the interposing portion of the protection element, on the edge of the bone.

The interposing portion may be positioned, when the protection element is attached to the elongated bone cutting tool or its frame, at the second extremity of the elongated cutting tool.

The first extremity may be directly driven by the cutting robot or the machinery. The second extremity may not be driven directly but moves by virtue of the driving of the first extremity.

It is an advantage that the protection element is positioned between the bone to be cut and the soft tissue. This ensures that the bone cutting tool will not damage the soft tissue. It is also an advantage of embodiments of the present invention that the protection between the bone and the ligament can be performed in cases where the use of a separate protection element installed independent of the bone cutting tool is difficult. The interposing element may be a bent portion for covering at least part of the extremity of the elongated cutting tool. The bent portion may cover both the top of the elongated cutting tool and a part of the side of the elongated cutting tool.

The protection system further may include an arm for holding the protection element, the arm being attachable to the bone cutting tool or a bone cutting tool frame and the arm being positioned for following alongside the bone cutting tool.

The arm typically may have a thickness equal to or smaller than the bone cutting tool, since the arm follows the bone cutting tool in the slot made in the bone. It is an advantage of embodiments of the present invention that the separator can be securely held while moving together with a bone cutting tool, and may provide effective ligament separation, even if the ligament is attached or stuck to the bone surface.

The interposing portion may comprise a soft tissue separator for separating the soft tissue from the bone.

It is an advantage of embodiments of the present invention that the ligaments can be separated from the bone, for example by detaching the ligament from the surface of the bone, separating them by the body of a soft tissue separator.

The soft tissue separator may be any of a sharp edge, a blunt end, a sharp circular shape, a mechanically moving cutting device, a mechanically vibrating edge, an electro-cautery knife or a pressure fluid jet.

The protection system may include a cooling system and/or an aspirator system for removing debris.

It is an advantage of embodiments of the present invention that water cooling can be used, which reduces thermal damage on living tissue, and/or an aspirator can be used, for reducing the chance of clogging the bone cutting tool due to the cuttings and remains of bone. Any or both of these systems may, for example, be included in the side arm or the cutting tool itself.

The protection element may include a bearing for supporting the second, typically non-driven, extremity of the bone cutting tool.

It is an advantage of embodiments of the present invention that as a result of support of the milling tool at the second extremity, a long and thin milling cutter can be used enabling small bone cuts to be performed by a single movement in which the cutting tool cuts the bone completely by moving from one end of the bone to the opposite end without returning.

It is an advantage of embodiments of the present invention that a rotating milling cutting tool with specific geometry and operational parameters can result in a significant reduction of the thermal load on the remaining bone compared to conventional techniques (e.g. oscillating saw). Together with the high accuracy and good flatness of the cut made possible with this invention, optimal boundary conditions to achieve good bone ingrowth for cementless implants are obtained.

It is an advantage of embodiments of the present invention that a rotating milling cutting tool with specific geometry and operational parameters results in significantly lower cutting forces and vibrations compared to conventional technique lowering the requirements for bone stabilization and reducing the error resulting from bone motion.

The protection element may have a width larger than bone cutting tool, and wherein during use. The protection element may follow in congruence with the bone cutting tool at a position outside the bone.

When the protection element is mounted on a side arm, such a side arm may be positioned aside the bone cutting tool inside a slit in the bone while the protection element or an interposing portion thereof is positioned outside the slit formed in the bone. It is an advantage of embodiments of the present invention that the arm supporting the separator can have a lower thickness than the cutting tool and can be positioned at the opposite side of the cutting side of the tool, enabling the arm to move together with the cutting tool in the slot created by the cutting tool. Doing so, an extra path for the arm connecting the protector to the frame resulting in increased soft tissue contact and therefore the risk of damaging is reduced. It is an advantage of embodiments of the present invention that good ligament protection is provided, by providing an smooth and homogeneous displacement thereof.

In some embodiments, the protection system comprises both a sensor for sensing the contact force of the protection element on the bone and a further sensor for sensing the force of the bone cutting tool on the bone.

It is an advantage of embodiments of the present invention that the contact between the separator and the bone surface can be monitored. This may enable automated or manual control ensuring a predefined contact between the protector and the outside of the bone even if the bone geometry is unknown. The latter can be obtained even when no navigation is used.

The present invention also relates to a bone cutting system including a bone cutting tool and a protection system as described above.

It is an advantage that a bone cutting system with embedded ligament protection is provided, which provides minimal damage to tissue surrounding the bone to be cut, by locally displacing the tissue away from the cutting portions of the bone cutting tool.

The bone cutting tool may be an elongated bone cutting tool and the protection element bends over the second, typically non-driven, extremity of the elongated bone cutting tool, covering a portion of the side.

It is an advantage of embodiments of the present invention that complete bone cutting as well as ligament protection is ensured.

The protection element may include a bent portion attached to the frame of the bone cutting tool by means of an arm. The bent portion may be hook shaped.

It is an advantage of embodiments of the present invention that the separator can easily follow the bone surface in a simple setup.

The bent portion may bend over the second, typically non-driven, extremity of the elongated bone cutting tool, such that the bent portion is covering at least part of a side surface of the elongated bone cutting tool. The elongated bone cutting tool may be a milling cutter.

It is an advantage of embodiments of the present invention that complete bone cutting as well as ligament protection is ensured.

The bone cutting system may include sensor feedback, e.g. for guiding the cutting process based on the sensed contact force between the protection element and the bone or between the cutting tool and the bone.

It is an advantage of embodiments of the present invention that the contact between separator and bone surface can be monitored and the cutting action may be adapted according to the measurement of the sensors, e.g. it may be stopped if loss of contact is detected or the cutting tool path can be adjusted to preserve contact between the separator and the bone or the cutter.

The bone cutting system may further include an adaptive cutting control. Such adaptive cutting control may include adaptation of the cutting as function of the obtained sensor feedback.

It is an advantage of embodiments of the present invention that the cutting and feeding speed may be adapted in accordance with the hardness of the bone, and thermal damage can be controlled.

The bone cutting system may furthermore comprise a navigation system for locating the bone and a robot for controlling the cutting tool path actively or passively.

The bone cutting system may comprise a controller for performing the cut automated based on information from the navigation system, the bone geometry and optional force sensors. Optionally, surgeon interaction information also may be taken into account.

The bone cutting system may be adapted for performing the cut manually, further including a mechanical guiding system connected to the bone, or to an external frame for guiding the system along predetermined directions. The movement of the cutting tool may be restricted to translation and rotation in the cutting plane by a mechanical guiding system connected to the bone, a robotic system or an external frame. The present invention also relates to a kit of parts including a bone cutting tool and a protection system as described above.

The present invention also relates to a protection system for a surgical bone cutting tool, the system comprising a protection element, the protection element being attachable or attached to the bone cutting tool or to a frame linked to the bone cutting tool in such a configuration that, during cutting with the bone cutting tool, the protection element follows in congruence with the bone cutting tool and the protection element including an interposing portion for, when attached to the bone cutting tool or a frame during cutting of a bone surrounded with soft tissue, being interposed between the soft tissue and the bone cutting tool, for preventing the bone cutting tool from cutting into the soft tissue.

In one aspect, the present invention also relates to a bone cutting system for cutting a bone of a subject for surgery, the bone cutting system comprising an elongated surgical bone cutting tool adapted for cutting the bone, the elongated surgical bone cutting tool having a first extremity for fixing the elongated surgical bone cutting tool to a cutting robot or machinery and a second extremity opposite thereto at an end of the elongated surgical bone cutting tool. The bone cutting system further comprises a protection system comprising a protection element attachable to the elongated bone cutting tool or a frame of the elongated bone cutting tool, wherein the protection element includes an interposing portion covering, when the protection element is attached to the elongated bone cutting tool or the frame of the elongated bone cutting tool, at least part of the second extremity of the elongated bone cutting tool, so that the interposing portion is being interposed between soft tissue surrounding the bone and the bone cutting tool during cutting with the elongated cutting tool, for preventing the bone cutting tool from cutting into soft tissue surrounding the bone. The protection element further comprises a supporting portion for receiving and supporting at least a part of the second extremity of the elongated bone cutting tool. Such supporting typically may be obtained through a contact, e.g. direct contact, between the supporting portion and the second extremity of the elongated bone cutting tool. Such supporting portion may advantageously be used for elongated bone cutting tools having a length of least 3 cm, preferably a length of at least 4 cm and a diameter between 2 and 5 mm, preferably a diameter between 3 and 4 mm.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
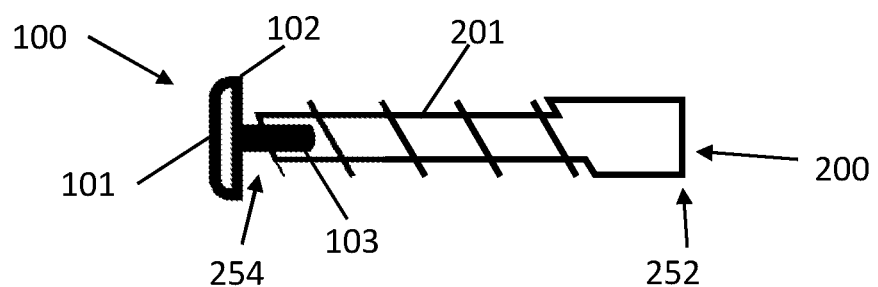
FIG. 1 illustrates an embodiment of a bone cutting tool including protection in accordance with embodiments of the present invention.

Some drawings do not explicitly show the sensor element of the bone cutting system, but focus on other standard or optional elements, features and advantages of bone cutting systems according to embodiments of the present invention. Nevertheless, as will be understood by the skilled person, the sensor may be integrated as shown in the other drawings or as described in the below detailed description of the illustrative embodiments.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

When in embodiments of the present invention reference is made to a bone cutting tool, reference may be made to a tool allowing to cut or to saw into bone in any suitable manner, such as for example by milling.

Where in embodiments of the present invention reference is made to a slot or slit in a bone, reference is made to the, often planar, cut that is made into the bone. This could also be referred to as a cutting plane.

Where in embodiments of the present invention reference is made to a cutting portion of the saw, reference is made to the part of the saw allowing—upon movement—to make the cut in the bone. In elongated bone cutting tools this typically is a part of the side surface of the elongated cutting tool. Where in embodiments of the present invention reference is made to the width of the bone cutting tool typically reference is made to its size that will determine the width of the slot made in the bone when cutting. For the example of the milling drill, this corresponds to the diameter of the drill, for the example of the saw this typically corresponds to the thickness of the saw blade. Where in embodiments of the present invention reference is made to the width of the protection element, typically reference is made to the size in the direction determined by the width of the slot that is made in the bone when cutting.

The present invention provides effective protection of the ligaments attached to or located next to a bone. The protection system according to embodiments of the present invention prevents the ligaments from being damaged with a bone cutting tool during bone surgery. Suitable bone surgery include arthroplasty, e.g. knee replacement, but the present invention is not limited thereto, and it could be applied to elbow surgery, hip replacement, and the like.

When cutting a portion of a bone, it is well possible that the bone cutting tool is introduced too deep, protruding through a side of the bone where ligaments rest. Damaging the ligaments can pose serious complications during the operation and afterwards during recovery. In particular, ligaments are anchored to bones along the bone shaft, but they may be attached or partially attached to the bones. This makes the ligaments very vulnerable to damages while cutting the bone.

Where in embodiments of the present invention reference is made to ligaments, tendons or soft tissue, typically either or all of these three tissues can be mentioned. Ligaments and tendons typically have the same structure, but ligaments are connecting bone to bone whereas tendons connect muscle to bone. Soft tissue is a collective of both but includes also other structures as the knee capsule which also needs to be protected during intervention.

In general, the devices of the present invention a protection system for a surgical bone cutting tool is described that comprises a protection element being attachable or attached to the bone cutting tool or to a frame linked to the bone cutting tool. The protection element thereby is in such a configuration that, during cutting with the bone cutting tool, the protection element follows in congruence with the bone cutting tool and the protection element includes an interposing portion for, when attached to the bone cutting tool or a frame during cutting of a bone surrounded with soft tissue, being interposed between the soft tissue and the bone cutting tool, for preventing the bone cutting tool from cutting into the soft tissue. When the bone cutting tool is an elongated surgical bone cutting tool, it typically has a first extremity for fixing the bone cutting tool to a cutting robot or machinery and a second extremity opposite thereto at an end of the elongated surgical bone cutting tool. The protection element then includes an interposing portion covering, when the protection element is attached to the elongated bone cutting tool or a frame of the elongated bone cutting tool, at least part of the second extremity of the elongated bone cutting tool, so that the interposing portion is being interposed between soft tissue surrounding the bone and the bone cutting tool during cutting with the elongated cutting tool, for preventing the bone cutting tool from cutting into the soft tissue, and wherein during cutting with the elongated cutting tool, the protection element follows in congruence with the bone cutting tool.

The devices of the present invention ensure protection of soft tissue during cutting. The protection is provided by a protection element, which overlaps and covers at least a portion of the bone cutting tool, in the case of an elongated bone cutting tool typically the extremity of the tool opposite to the end that is attached to the actuator of the tool. The extremity where the tool is attached to the actuator of the tool, i.e. to a cutting robot or machinery, is typically referred to as the first extremity. The extremity where the protection element is used, typically is referred to as the second extremity. Typically such extremity is not directly driven, but moves due to the driving at the first extremity. In embodiments where the cutting tool is an elongated cutting tool, the second extremity typically is the top of the elongated cutting tool. The protection element, which may be a separator, also moves in congruence, i.e. in the same direction and simultaneously with, the bone cutting tool, following the bone cutting tool on its cutting path, through the bone. Thus, the protective element can be slid or wedged between soft tissue and bone, so the protective element is interposed or interlayered between the soft tissue and cutting tool. Thus, soft tissue like the ligaments are away from the cutting portion of the bone cutting tool. This way, the bone cutting tool does not reach the ligaments, when cutting is performed. It is to be noted that the "cutting path" is the path that results in a slot or cut through a body. The cutting path will be formed along a path, following the average movement of the cutting tool, also referred to as "subsidiary movement". The average motion of the cutting tool does typically not follow the "cutting motion", or "main movement" of the tool, which is the motion of the tool resulting in material removal from the body; in general the subsidiary movement and the cutting motion will be done in different directions.

In a first aspect, the present invention relates to a bone cutting system including a protection system. The protection system comprises a protection element that can cover a portion of a bone cutting tool or saw, and can be moved simultaneously with the bone cutting tool following its cutting path. FIG. 1 shows a simple embodiment illustrating a protection system 100, where a plate acting as protection element 101 has an edge 102 and an attachment portion 103 linked to a bone cutting tool 200, in this case a mill that cuts with a sidewise motion with its cutting portion 201. In some embodiments, the protection element 101 is an integral part of the bone cutting tool 200. The protection element also may function as soft tissue separator for separating the soft tissue from the bone, as will be described later. For illustrative purposes, the first extremity 252 and the second extremity 254 is shown in FIG. 1.

The plate acting as protection element may be attached to a central axle of the drill 200 so it does not rotate with the drill. If the diameter of the drill does not allow the presence of an immobile central axle, the attachment portion 103 may include bearings, so the rotation is reduced as compared to the drill. In other embodiments, both the drill and the plate may rotate. The rotation of the plate may be used to separate the ligament from the bone, without sectioning the ligaments.

In some embodiments, the protection element 101 may be softer than bone, so the plate does not cut or damage the bone, but harder than the soft tissue.

In some embodiments, the protection element bends over the second extremity of the elongated bone cutting tool, covering a portion of the side of the elongated bone cutting tool. The latter will be illustrated more specifically e.g. in FIG. 4, FIG. 9, FIG. 13, FIG. 18 and FIG. 19.

Figure 2:
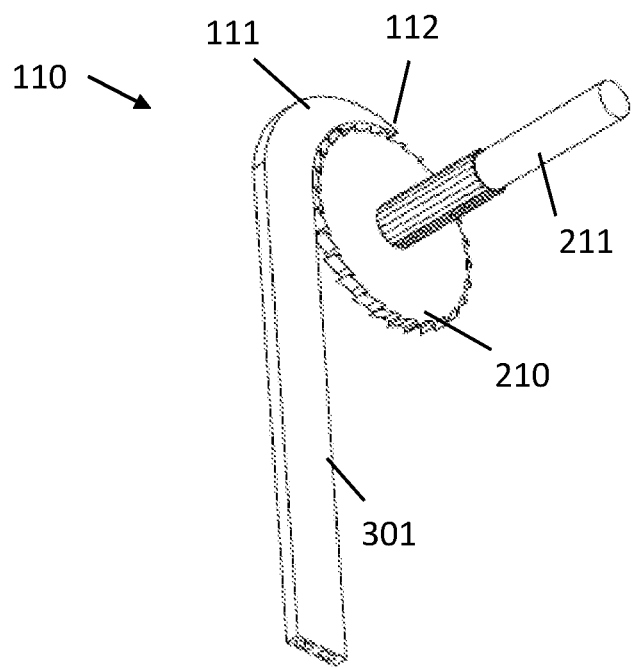
FIG. 2 illustrates an embodiment of a bone cutting tool with a protection system in accordance with embodiments of the present invention.
Figure 14:
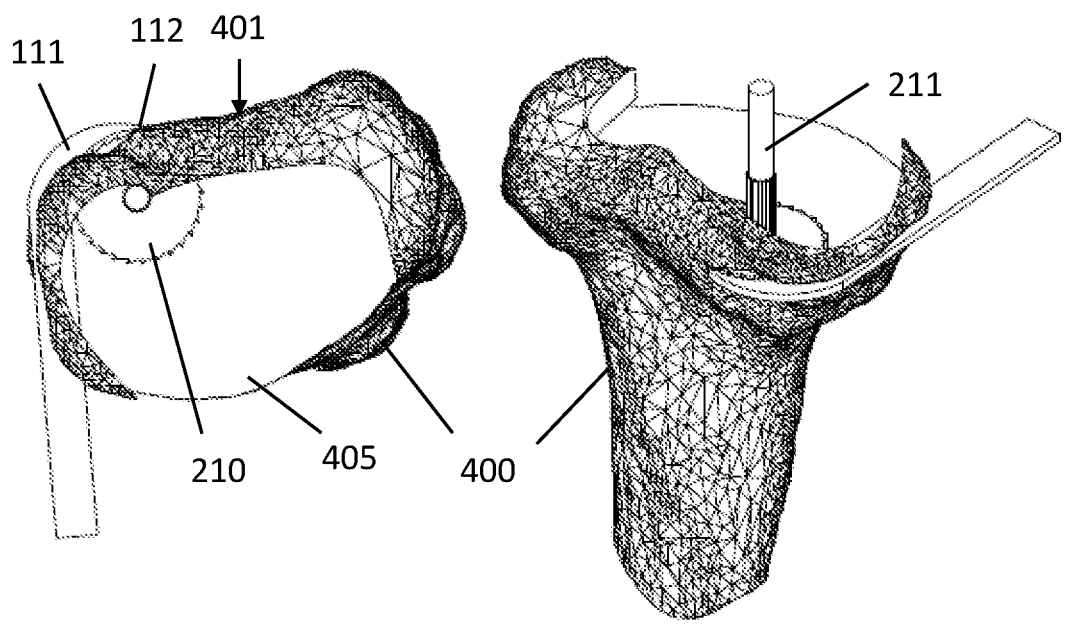
FIG. 14 illustrates the embodiment of FIG. 2 while removing a bone wall.

FIG. 2 shows another embodiment of protection system, where a bent portion 111 acts as separator. An arm 301 holds the bent portion 111. FIG. 14 shows an example of application of such embodiment, where a circular saw cuts through a wall 401 of the bone 400. In this case, a portion of the bone is first removed without the separator being attached and while maintaining a safe distance between the saw and the bone wall 401. As a result of the cutting shaft 411, a part of the upper bone is already removed in this step. Then, the wall 401 is cut through (this is further explained in the section "Two-step cutting and one-step cutting" below). The two step cutting may be used when the diameter of the sawblade is too small to add the protection element from the start. The bent portion 111 covers part of the cutting edge of a circular saw 210, which can be used to remove the bone wall 401 of a bone 400, e.g. of the proximal tibia, the distal femur, the femoral head, or head of humerus. The arm and bent portion are movable, following the cutting path of the saw. The tip or point 112 of the bent portion, acting as edge of the separator, overlaps slightly the edge of the bone, being interposed between the soft tissue and the bone, so the saw does not touch the soft tissue when removing the bone wall 401. The present invention is not limited to the point of a bent portion, and any suitable edge of a separator can be used.

The fact that the separator follows the cutting path has an effect that it only locally detaches and stretches the ligament away from the cutting area, which is relatively small. Thus, the ligament is not only protected, but also submitted to low strain during the cutting procedure.

The separator may be based on different separation techniques, such as for example the use of a blunt end, the use of a sharp pointed shape, the use of a sharp circular shape, the use of an electrocautery knife, the use of a pressure fluid jet, the use of a mechanically moving cutting device or the use of a mechanically vibrating edge.

Arm Attachable to Frame of Cutter

Figure 3:
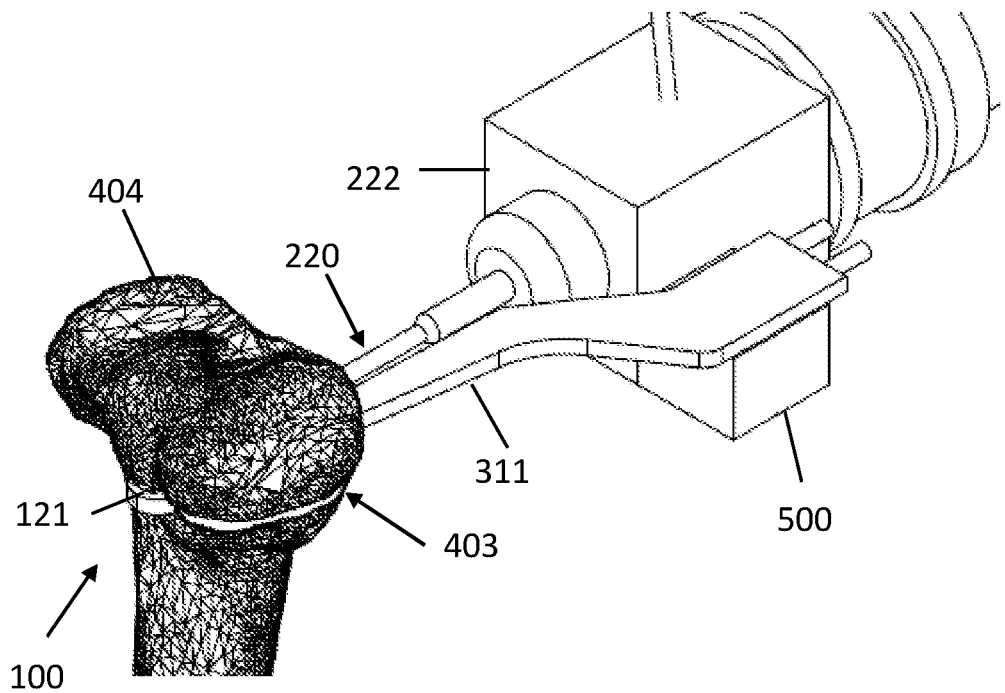
FIG. 3 and FIG. 4 illustrate different perspectives (FIG. 4 shows a section view with the upper part of the bone being removed from the drawing for better visualization) of a bone cutting tool with a protection system while removing a bone wall in accordance with embodiments of the present invention.

FIG. 3 shows a preferred embodiment of cutting system with protection system, where a bent portion 121 acts as separator for covering the head end of the milling cutter 220, which is in this case the bone cutting tool, and an arm 311 that holds the bent portion 121. The arm 311 moves with the same orientation and direction as the milling cutter 220 and simultaneously with it. For example, the arm 311 may be removably or permanently attached to the frame 222 of the actuator of the cutter as shown in FIG. 3, the present invention not being limited thereto; for example, both arm and cutter may be simultaneously moved following the same path by a robot or the like.

Figure 4:
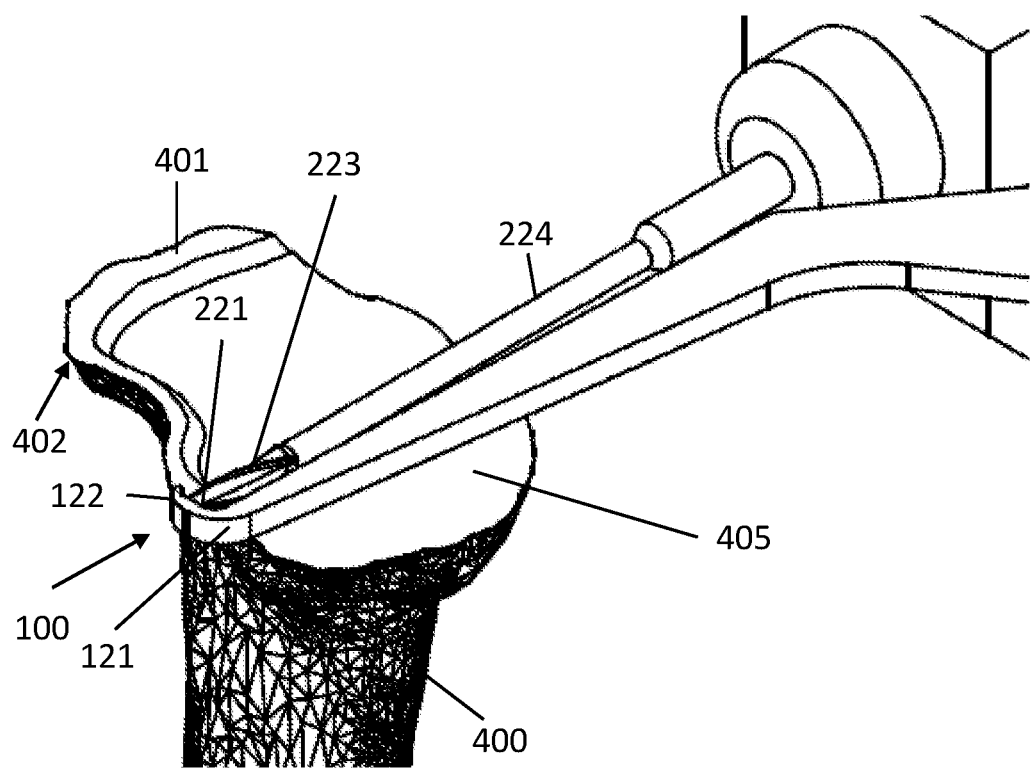

FIG. 4 shows a different perspective (a section view along the slot 403 in FIG. 3) of the bent portion and milling cutter of FIG. 3, where it can be clearly seen that the bent portion 121 slightly overlaps the external surface 402 of the bone

400. The point 122 of the bent portion 121 is placed in contact with the bone, and it acts as edge of the separator. The bone cutting tool 220 follows a cutting path removing the bone wall 401, and the bent portion 121, while moving together with the bone cutting tool 220, can wedge between ligaments and bone, separating and lifting the ligaments from the region of the bone before the region is cut. In other words, the edge of the bent portion 122 drags over the external surface 402 of the bone 400, and any ligament present there is separated from the bone, and it slips over the bent portion 121. Thus, the head end 221 of the milling cutter 220, which is completely shrouded by the bent portion 121, is separated from any ligaments by the bent portion 121, so the bone cutting tool 220 does not damage the ligaments.

Arm and Cut Slot

Figure 5:
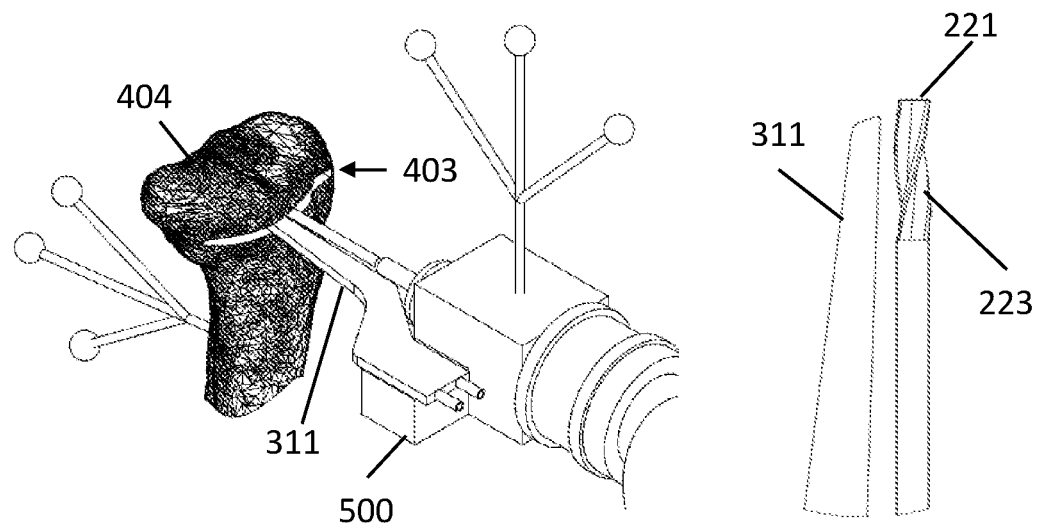
FIG. 5 illustrates the bone cutting tool of FIG. 3 and FIG. 4 while performing slot cutting, with the protection element removed.

FIG. 3 and FIG. 5 shows the possibility of slot cutting using a separator with an arm which fits a slot in the bone provided by a bone cutting tool. This is further described in the "Two-step cutting and one-step cutting" section below. The thickness of the arm 311 can be the same, preferably thinner, than the gap 403 of the cutting slot in the bone. This way, the arm and bent portion 121 (which is partially hidden in FIG. 3 by the remaining upper part 404 of the bone) can follow the cutting path of the bone cutting tool while the bone cutting tool is removing material from a bone (or bone wall) with ligaments at its external surface. The point 122 of the bent portion 121 separates ligaments from the bone, protecting them from the bone cutting tool, as also explained with reference to FIG. 4.

Sensor in Protection System

Figure 15:
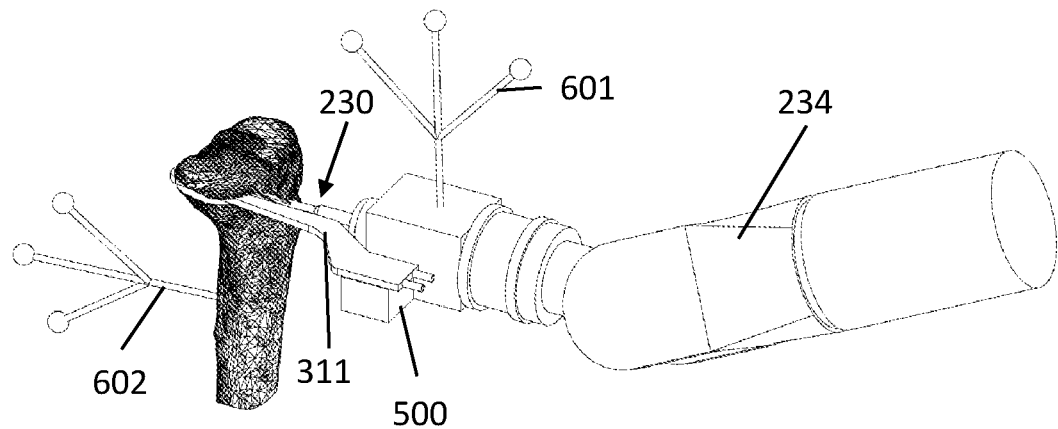
FIG. 15 illustrates a bone cutting tool including a protection system, including means for providing automated cutting, in accordance with embodiments of the present invention.

The protection system may comprise a sensor for sensing forces on the bone. The sensor may be provided for sensing forces of the protection element on the bone or for sensing forces of the bone cutting tool on the bone or a combination of both. Where the sensor is provided for sensing forces of the protection element on the bone the sensor may be provided for sensing forces of the interposing portion or of the arm of the protection element on the bone. Sensing forces may comprise directly sensing forces by means of a force sensor or indirectly sensing forces of a sensor from which the force on the bone may be derived such as for instance a pressure sensor. The sensor may be a sensor or a combination of sensors for sensing a combined force from which the contact force of the protection element on the bone can be derived. In some embodiments of the present invention, the separator and/or the arm may include a sensor, for sensing forces applied on the separator. FIG. 3 and FIG. 15 show an example thereof. A sensor 500 is included between the arm 311 and the frame 222 of the bone cutting tool. In other embodiments, the sensor also be included along the arm or in the protector/bent portion, for sensing forces on the arm, or on the bent portion 121, etc. In some embodiments, also another sensor, sensor 511, can be used to extract the bent portion bone contact force.

In some embodiments, the pulling force on the separator can be sensed, this may include for example the force that the bent portion 121, or more in particular its point 122, applies on the bone surface 402. The present invention is not limited to pulling force, and other forces and torques can also be measured. The user may receive feedback from the sensor, which can be used to find the edge of the bone, for example in combination with data related to the bone shape, e.g. obtained from a CT scan. Additionally or alternatively, the sensed forces may be used to adjust cutting parameters, as it will be explained later. The sensor may be used to facilitate an automated robotic system allowing sensing the edge and cutting the bone automatically.

Water Cooling and Debris Removal

Figure 6:
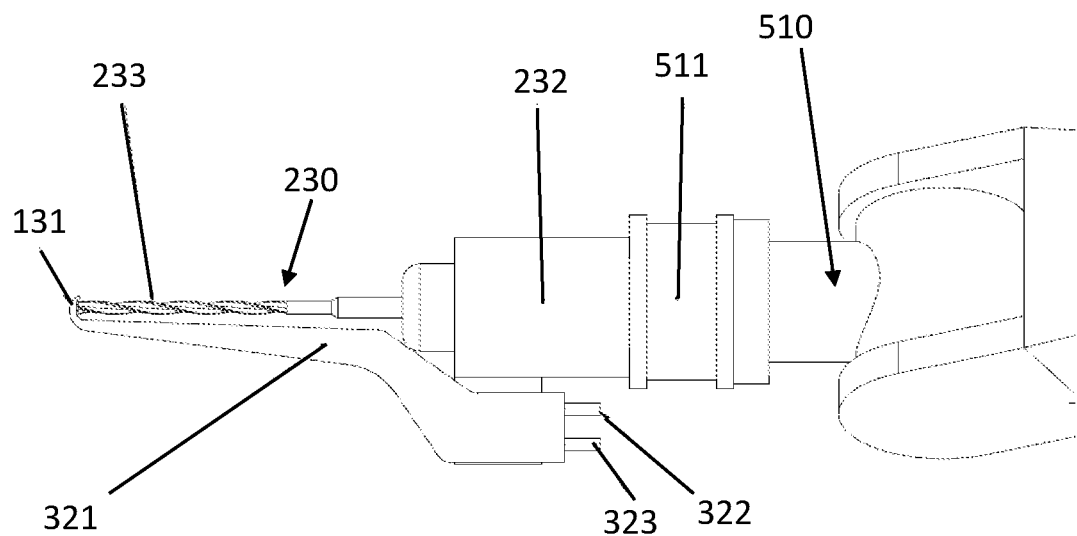
FIG. 6 illustrates a bone cutting tool with a protection system in accordance with embodiments of the present invention.
Figure 11:
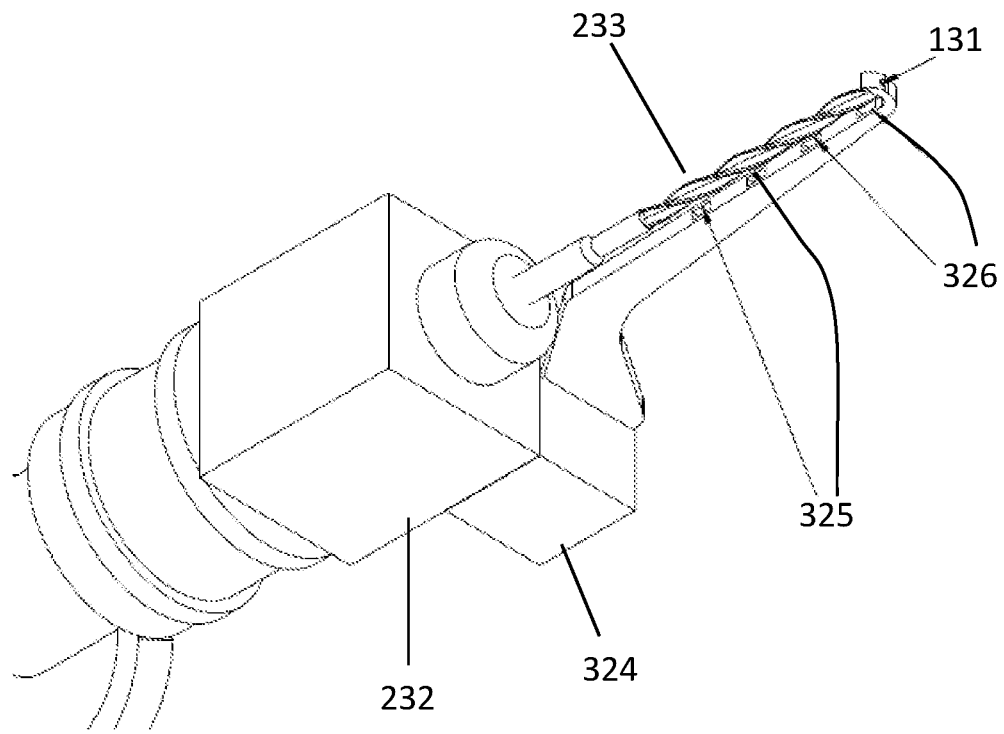
FIG. 11 illustrates a different perspective of the bone cutting tool shown in FIG. 10

In some embodiments of the present invention, the arm and/or the separator includes means for removing debris. For example, as shown in FIG. 6 and FIG. 11, the arm 321 may include a chip removal channel 322 (e.g. an aspirator) and/or conduits 323 for fluids, for example for introducing water and removing debris. FIG. 11 shows the intakes 325 of the chip removal channel 322 (FIG. 6), and the outlets 326 of the conduits 323 for water or other fluids (FIG. 6). Such fluids may be used for cooling and/or cleaning. Water may be used as coolant, for reducing the temperature of the bone cutting tool and the thermal stress of the bone and its cells, so the conduits 232 and outlets 326 may form a cooling system. In some embodiments, the conduit for introducing a fluid to, e.g., remove debris may be positioned in a central portion of the mill and thus may be provided through the cutting part of the bone cutting tool.

Detachable Separator

The protective element (e.g. separator), according to some embodiments of the present invention, may be detachable. For example, the bent portion 121 may be detachable from its arm 311 as shown in FIG. 5, thus revealing the head end 221 of the milling cutter 220, which normally is not accessible due to the protection element. In alternative embodiments, as shown in FIG. 6 and FIG. 11, the bent portion 131 is attached to its arm 321, but the arm 321 is detachable from a frame 232, for example the arm 321 may include a bridge piece 324 that detachably anchors the arm 321 to the frame 232 or chassis of the actuator of the cutter 230. This allows different cutting and drilling possibilities, where the bent portion is only used when the external wall of the bone needs to be removed.

Wide Separator

Figure 12:
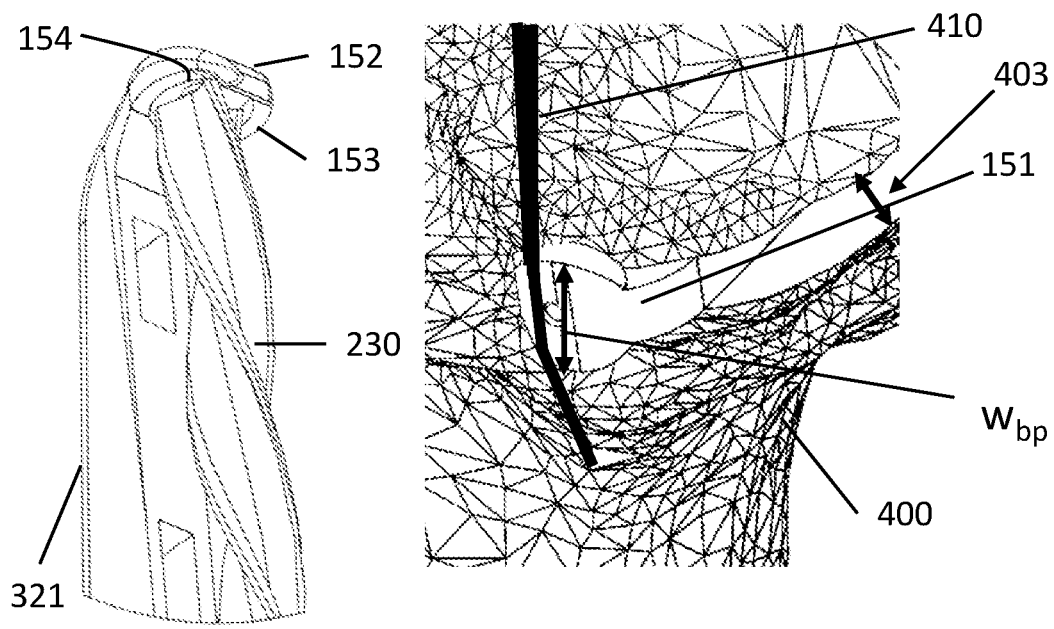
FIG. 12 illustrates a bone cutting tool including a protection system in accordance with embodiments of the present invention, and the bone cutting tool being used.

In some embodiments of the present invention shown in FIG. 12, the bent portion 151 may be chosen so its width $w_{bp}$ does not fit the width 403 of the cutting slot—the width 403 of the cutting slot typically corresponds roughly with the width of the elongated bone cutting tool by which the slot is made—left by the bone cutting tool in the bone. During slot cutting, the bent portion must remain outside the bone, while the bone cutting tool 230 and the arm 321 are inside the bone. The bent portion 151, being wider than the slot, ensures a better shielding between the soft tissue and the cutting tool. For example, the part of the bent portion 151 which widens from the arm may form a protrusion 153. This protrusion 153, in combination with the point 152 of the bent portion 151, can be used as a guide for cutting. This improves protection of the ligament 410, obtaining smoother and more homogeneous strain on the ligament 410 and more separation from the cutting portion of the bone cutting tool.

Materials

In embodiments of the present invention the bent portion and/or the arm may be bio-compatible. They may be metallic, e.g. a steel bent portion or arm, and/or including materials with disinfectant, anti septic and/or antimicrobial properties.

In a second aspect, the present invention relates to a bone cutting system, including a separator according to embodiments of the first aspect, and a bone cutting tool.

The bone cutting tool may be a radial saw, as shown in the cutting system 110 FIG. 2. Other bone cutting tools, such as for example an oscillating or reciprocating saw or other cutting techniques with mechanically moving cutting edges to perform bone removal, may be used. The separator covers part of the cutting edge of the saw with respect to the cutting path, so it is ensured that the separator enters in contact with the ligaments and separates them from the bone before the saw reaches that part of the bone.

In preferred embodiments, a milling cutter is used. The milling cutter 220 includes a cutting portion 223 and a shaft 224 (shown in FIG. 4), the shaft being linked to an actuator in the frame 222 (shown in FIG. 3) for rotating the cutter 220 about its own axis. The cutting portion may be a drill, mill ball, etc. In particular embodiments of the present invention, the milling cutter is an end mill. FIG. 1 and FIG. 3, FIG. 4, FIG. 6 to FIG. 13 and FIG. 15 to FIG. 17 show exemplary embodiments of a bone cutting system according to embodiments of the present invention, including milling cutters whose head end are overlapped and shrouded by a bent portion acting as separator.

Geometry of the Separator with Respect to the Bone Cutting Tool

Figure 7:
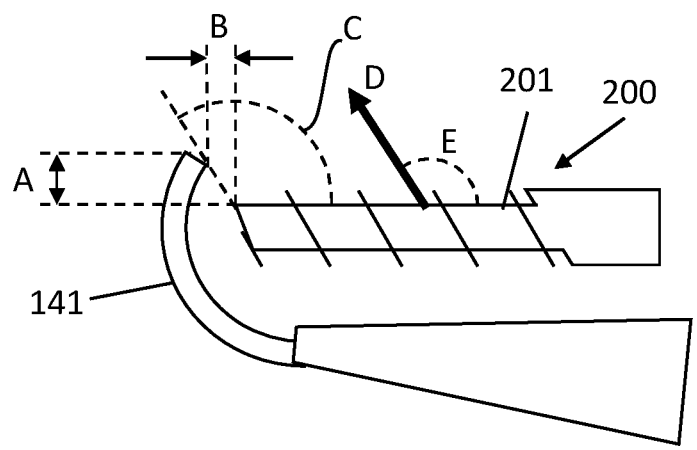
FIG. 7 to FIG. 9 illustrate different embodiments of a bone cutting tool including a protection system in accordance with embodiments of the present invention, with different degrees of overlapping.
Figure 8:
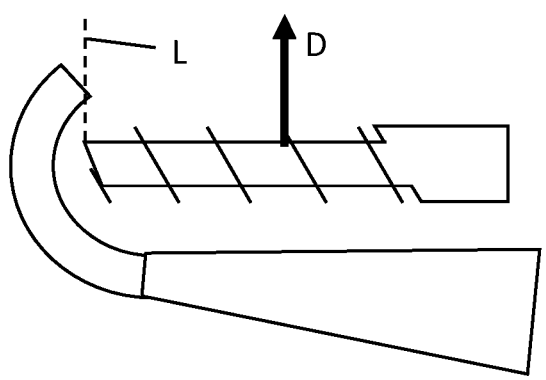
Figure 9:
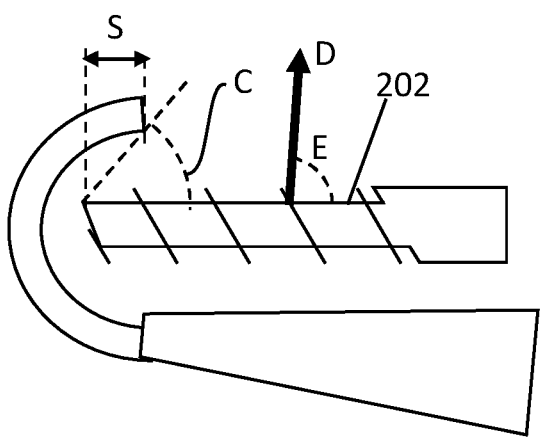

In some embodiments of the present invention, the separator overlaps the cutting portion of the bone cutting tool. For example, the separator may form a wedge or bent portion or the like, extending over the cutting portion of the bone cutting tool, specifically the part of the bone cutting tool that contacts the bone. The bent portion may extend a predetermined distance A from the region of contact between the bone and the bone cutting tool 200, as shown in FIG. 7. In some embodiments, the distance A is at least 1 mm.

In preferred embodiments, the separator shrouds a part of the cutting portion of the bone cutting tool. For example, it may cover part of the cutting portion of a milling cutter, with respect to the cutting direction D. The cutting direction D is the direction that takes the cutting path, and it is preferred that the cutting direction is parallel to the outer surface being cut. In some embodiments, the point of the bent portion 141 and the line joining said point with the end head of the bone cutting tool 200 forms an angle C with the axis of the cutter. On the other hand, a cutting angle E between the cutting direction D and the cutter axis can be defined. In preferred embodiments, the cutting angle E is larger than the protection angle C; C<E. This ensures a proper shrouding. Even if the cutting direction deviates slightly from the tangent direction of the outer bone surface, this configuration still provides protection to the ligaments.

It is shown in FIG. 7 that, if the angle C is obtuse, there is a distance B between the separator and the bone cutting tool, facing the perpendicular of the cutter axis. This is less preferred, because the angle E needs also to be obtuse, and milling cutter, especially end mills, are optimized to cut in a cutting direction D perpendicular to the cutter axis. In some embodiments, the angle C is square, so the distance B becomes zero, as shown in the total overlap line L in FIG. 8. This allows a direction D perpendicular to the axis. In preferred embodiments, the angle C is negative, and the distance S is the distance that the bent portion covers the cutting portion 201 with respect to the cutter axis. Thus, even for cutting angles E that are obtuse (which may happen during intervention due to irregular surfaces), the bent portion will still cover the end head of the bone cutting tool as long as C<E, allowing ligament separation and protecting the ligaments from the bone cutting tool.

It is noted that E is not a fixed angle, and may change for taking into account differences in the direction of cutting during an intervention, due to the irregular surfaces. By ensuring that C<E, for example by providing a small protection angle C, good overlap between the bent portion and the milling cutter is ensured, because even for relatively large changes of direction D, the cutting angle E can easily be kept larger than the protection angle C.

This theory can also be applied to circular saw, as in FIG. 2. In that case, the line being tangent to the circle described by the rotational movement of the cutting edge and including the point of the bent portion forms an angle C with an arbitrary line; the cutting direction with respect to the same arbitrary line should form an angle E larger than C as before, in order to ensure proper shrouding.

In preferred embodiments, the cutting direction D is parallel or almost parallel to the external surface of the bone wall. The bone cutting tool should be redirected accordingly. The axis of a milling cutter, for example, should be kept perpendicular to this direction. The particular geometry of the separator (e.g. the angle B, the distance A or the overlapping distance S) ensures good protection and separation of ligaments even if the cutting direction deviates from this direction in practice.

Sensor in Cutting System

The bone cutting system may comprises a sensor for sensing forces on the bone, for instance contact forces of the protection element on the bone or contact forces of the elongated bone cutter on the bone or a combination of both.

Where the sensor is provided for sensing forces of the protection element on the bone, the sensor may be provided for sensing forces of the interposing portion or of the arm of the protection element on the bone. Sensing forces may comprise directly sensing forces by means of a force sensor or indirectly sensing forces of a sensor from which the force on the bone may be derived such as for instance a pressure sensor. The sensor may be a sensor or a combination of sensors for sensing a combined force including the contact force of the protection element on the bone, for instance a sensor for combined measuring a force of the elongated cutting tool on the bone and a force of the protection element, e.g. the interposing portion of the protection element, on the edge of the bone.

The sensor may be located in the protection system itself, in the elongated cutting tool, in the frame connecting the cutting tool and the protection system to the robot or in the robot itself. The sensor may be a sensor or a combination of sensors for sensing a combined force including the contact force of the protection element on the bone, for instance a sensor for combined measuring a cutting force and a force of the protection element, e.g. the interposing portion of the protection element, on the edge of the bone.

As explained with reference to embodiments of the first aspect, sensors 500 (sensing units, sensor modules or the like) may be added, for sensing the force applied with the separator (e.g. bent portion 121, 131) on the surface of the bone. This can be used in combination with a mapping of the bone surface, e.g. a CT scan, to pinpoint where the cutting is taking place, and to signalize if the force is reduced.

In some embodiments, sensor feedback can be used in the cutting system of the present invention. FIG. 5 shows a cutting system including a sensor 500 which senses the contact force of the bent portion 131 on the bone surface, through the frame. In an alternative embodiment, also a separate load cell 511 is included for sensing the force on the spindle. Sensor 511 can for example be a 6 axis force torque transducer performing a combined measurement of the cutting force and the force of the bent portion on the edge of the bone. The force coming from the cutting process then can be separated from the bent portion force by calculation. In some embodiments only a 6 axis load cell may be used for measuring the combined force. In some embodiments, an algorithm can be used to differentiate between bent portion-bone contact force and cutting forces. In some embodiments only the bent portion force may be sensed with a force sensor. In some embodiments both a 6 axis load cell and a force sensor may be used. The cutting and feeding speed of the milling cutter can be controlled, to adjust the intervention to different hardness and densities of bones, or of bone areas. For example, the speed may be adapted for providing a fast cutting, while reducing thermal load and reducing or avoiding thermal damage of the bone. For example, if loss of contact is detected, the bone cutting tool may stop.

Reducing thermal damage of the bone allows faster recovery, and it allows using cementless implants with porous surface, promoting bone growth through the porous, improving anchoring to the bone.

The low temperature increase may be also improved by a careful choice of parameters related to the bone cutting tool per se, such as size of the cutting portion, type of blade, helix angle, number of teeth (also referred to as flutes), etc.

According to some embodiments, typically embodiments wherein the cut is performed in a single step although the invention is not limited thereto, the cutting tool advantageously has a minimal cutting length of 45 mm or more, e.g. 50 mm or more and a cutting tool diameter between 2 mm and 8 mm, e.g. between 3 mm and 5 mm.

The sensor for directly or indirectly measuring forces of the elongated cutting tool on the bone may be located on any location between the elongated bone cutting tool and the fixed environment. Preferably, the sensor is located close to the cutting tool. The sensor may for instance be located between the motor of the bone cutting tool and the end effector of the robot, i.e. last part of the robot where tools are mounted on, such as for instance shown as part 511 in FIG. 6. The sensor may be integrated in the robot arm, for instance somewhere in between the base of the robot and the end effector. Other locations are possible such as for instance integration in a part of the protection system of the bone cutting system, in the motor or any other location.

FIGS. 5 and 6 show a preferred embodiment of a sensor implementation according to embodiments of the present invention. In FIGS. 5 and 6 the protection element is mounted to the end effector assembly after the sensor to measure the cutting forces 511. This implies that forces exerted on the protection element (131, 321) are added to the measurement of sensor 511. If the protection element was connected to the end effector 510 before sensor 511, forces exerted to the protection element are not measured by sensor 511.

In the first case (connection after sensor 511) the cutting forces are added to the contact forces of the bone on the protection element in the measurement of sensor 511. Mathematically those two forces could be extracted separately from the measurement of 511 to obtain the cutting force and the contact force between the bone and the protection element. In the second case, the protection element is connected before sensor 511, an extra sensor between the protection element tip (that makes contact with the bone) and the end effector is preferably added. An additional sensor may also be provided in the first case where the protection element is connected after sensor 511. Such an additional sensor between the protection element tip and the connection to the cutting motor assembly 231 (or straight to 511) is beneficial as the contact force can be determined with greater accuracy and reliability. The additional sensor may be integrated everywhere between the protection element tip (where the protection element makes contact with the bone) and the location where the frame (321) is mounted to the end effector assembly. In FIG. 3 and FIG. 5, the sensor 500 is placed at the base of frame 321. Alternatively the sensing element could be integrated further in the frame 321 or even in the bend portion or tip 131 of the protection element.

In the preferred embodiment, the sensor measures at least the force in the normal direction of the protection tip to bone contact. Choosing the direction deviating from the normal is possible but less optimal. Measuring the force in more than 1 direction and possible including torque measurements is an option to obtain even more detailed contact information.

Alternatively to contact force measurements, the detection of the location of the edge of the bone could be done by other sensing systems. The protection element could be equipped with and alternative sensing system to determine contact between the element and the bone or to measure the location/distance between the bone and the device. For example a pressure sensor or distance sensor could be used.

Sensor 511 used to measure the cutting forces may measure the force on the bone in at least one direction, preferably the direction of the principal cutting speed direction. But the sensor can be expanded to measure forces in all 3 orthogonal directions and torques around these 3 orthogonal directions to have a sensor that measures forces and torques in all 6 degrees of freedom (also called 6 DOF or universal force sensor). Measurement of forces and torques in more than one direction can increase the accuracy of the cutting force measurement and can determine the cutting force in the non-principal moving directions too.

As explained earlier, the sensor may be a force sensor or any other sensor from which the force on the bone can be derived.

Optical Bone and Robot Registration

To enable robotic controlled bone cutting, the position of the bone preferably needs to be known with respect to the robot. A three dimensional tracking system, e.g. a tracking system with optical camera, which is able to track the position of beacons, e.g. optical marker sets, is used. A beacon 602, e.g. optical marker set, is for instance rigidly attached to the bone and another beacon 601 is for instance rigidly attached to the cutting robot as shown in FIG. 15. After attaching them, the position of the bone to the beacon fixed on the bone 602 is defined by the bone registration. In this process a series of points on the surface of the bone are measured by moving an optical pointer over the bone. Afterwards the shape of the bone, obtained from a CT scan, is fitted on the measured points. This calculation gives the position of the bone with respect to beacon 602. By combining this information with the measurement of the position of the beacon by the 3D tracking system, the location of the bone with respect to the camera is known.

To know the exact position of the robot with respect to the beacon on the robot 601, the robot performs multiple rotations around a known point. By tracking the movement of the beacon attached to the robot, the exact location of the robot with respect to the beacon on the robot can be calculated. Now the position of the robot with respect to the camera reference system is also known. As the position of the robot and bone is known in the camera reference system, the position between the bone and the robot is determined and the robot controlled cutting can start.

All the movements of the cutting tool (attached to the robot) are determined with respect to the bone. Bone movements can be followed by the robot to ensure the correct position of the cutting tool with respect to the bone.

Determine the Location of the Bone Edge/Contour

In embodiments of the present invention, the bone cutting system may comprise a sensor for sensing the contact between the bone and the protection system. This information may be used to sense the edge of the bone and to follow the bone contour more closely as compared to prior art systems. Such information may for instance be used in combination with data related to the bone shape, e.g. obtained from a CT scan or shape model.

Figure 20:
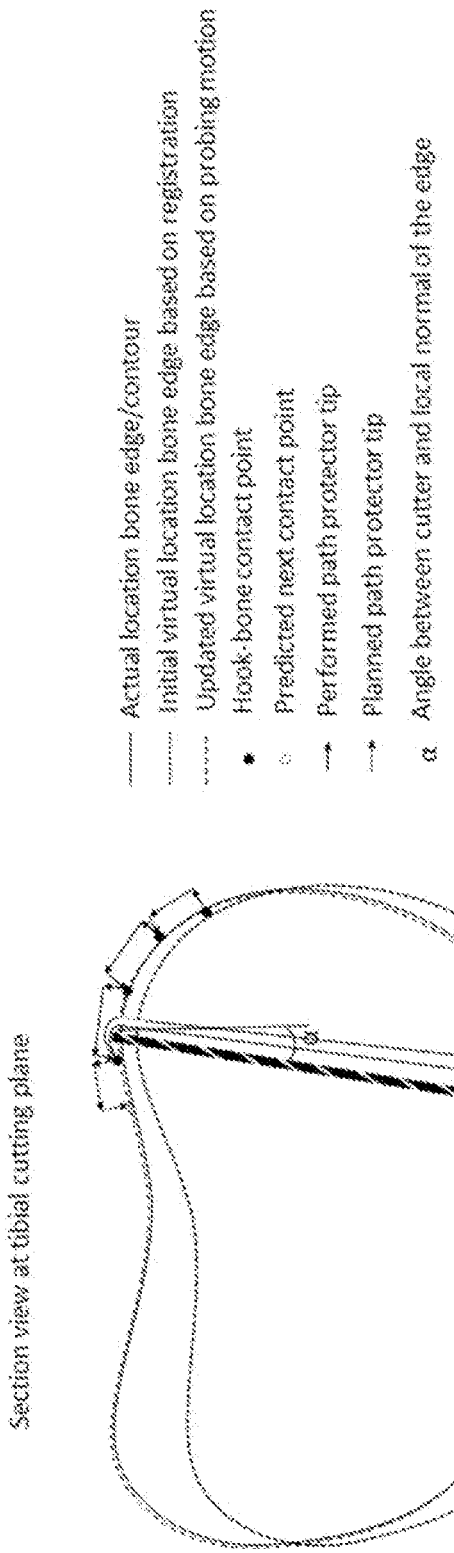
FIG. 20 illustrates an embodiment of a bone cutting system according to the present invention performing a bone edge determination.

FIG. 20 shows an embodiment of a bone cutting system according to the present invention where the edge of the bone is sensed. The interposing portion of the protection element, e.g. the soft tissue protecting hook 131, performs a probing motion along the edge of the bone. The contact between the protection element 131 and the bone is sensed by a sensor of the protection system, e.g. a load cell that is integrated in the protector support mounting. The position at which the bone is sensed is used to update the actual bone location and the derived path of the cutter-protector assembly. This technique enables the compensation for small segmentation and registration errors. Experimental tests showed that the real physical bone contour location could be predicted three times more accurate. The error on the location of the real physical contour was in one exemplary test 1.51 mm (SD=0.31) without active bone contour following. With active bone contour following, the error on the prediction of the actual bone contour decreased to 0.44 mm (SD=0.29).

An example of a probing motion of the protection element 131 will be described hereafter and shown in FIG. 20. The exemplary probing motion is a repetitive motion comprising the following steps:
1. the protecting hook 131 moves towards the bone surface
2. If contact between the hook and the bone is sensed by the force sensor, the position of this point is measured and the movement stops
3. The hook moves in the opposite direction (away from the bone surface) till a distance of e.g. 1-3 mm
4. The hook moves along the bone maintaining the same distance (as defined above) from the bone. To perform this movement, the shape of the bone (CT based, or based on shape models) is used. During this step, the bone will be cut.
5. When the hook moved a predefined distance further along the circumference of the bone (e.g. 1-20 mm) the movement along the circumference of the bone stops and the protecting hook will move again towards the surface of the bone
6. Back to step 1

This process repeats till the resection is complete. The measured points of step 2 are used to optimize the prediction of the actual bone position. In the beginning, the location of the bone is solely defined based on the bone registration process but this is not perfectly accurate as errors during the registration process are inevitable. Also the shape of the bone is not perfect. If the shape is based on a CT scan, the accuracy is limited by the scan resolution and the segmentation process an if the shape is based on shape models, the accuracy is limited by the model and the amount of input point. The algorithm to adjust the location of the virtual shape/contour of the bone is designed to minimize the local error at the position of the protecting hook. The local accuracy of the bone location is of most importance as the future path of the protection element is determined based on this information. During the future movement of the protection element, the element should move as close as possible along the circumference of the bone while avoiding penetration of soft tissue and collision with the bone.

Use of Bone Edge Location Information

In an active robotic system, the robot performs the cutting operation completely automatically. In such a system, the information about the contact measurements is used to optimize the estimation of the bone location to adjust the plan of the robot to make sure that the protection element follows the edge of the bone as closely as possible without colliding with the bone.

In a semi-active robotic system, a surgeon works actively together with the robot to perform the cutting action. In a first possible variant, the surgeon can move the robot by hand but the robot will limit the movement to a safe range of motion to make sure that the cutting tool stays within the correct plane and that the cutting tool does not penetrate soft tissue. In this case the information about the bone contact can again be used to optimize the estimation of the (local) bone location and to adjust the safe range of motion accordingly. Furthermore, haptic (vibrations, restraining force), visual or auditive feedback can be given to the surgeon when contact with the bone is made to support the surgeon in guiding the tool in the correct direction.

In another semi-active variant, no robotic arm is used and the tool is moved manually with the help of a mechanical support or mechanism to guarantee that the tool stays within the correct cutting plane. To make sure that the protection device follows the edge of the bone accurately, an active movement in one or more directions is imposed on the protection device, which will move together with the cutter. This way, the surgeon moves the tool along the cutting plane following approximatively the edge of the bone while the protective element moves in the longitudinal direction of the cutter to perform a probing motion along the edge of the bone. This way, the protection element can follow the edge of the bone closely by compensating errors in the movement of the surgeon. The system can give feedback to the surgeon, e.g. to keep the device in the center if its range of motion.

In a manual operated variant, the manual tool can be transformed to a smart device by adding this measurement. Feedback of the contact between the protection element and the bone can be given to the surgeon by haptics (vibrations), a visual or an auditive signal to support the surgeon in guiding the tool in the correct direction. Furthermore the feedback can be integrated in a surgical navigation system, possibly with augmented reality, to provide graphical/visual feedback to the surgeon.

Figure 21:
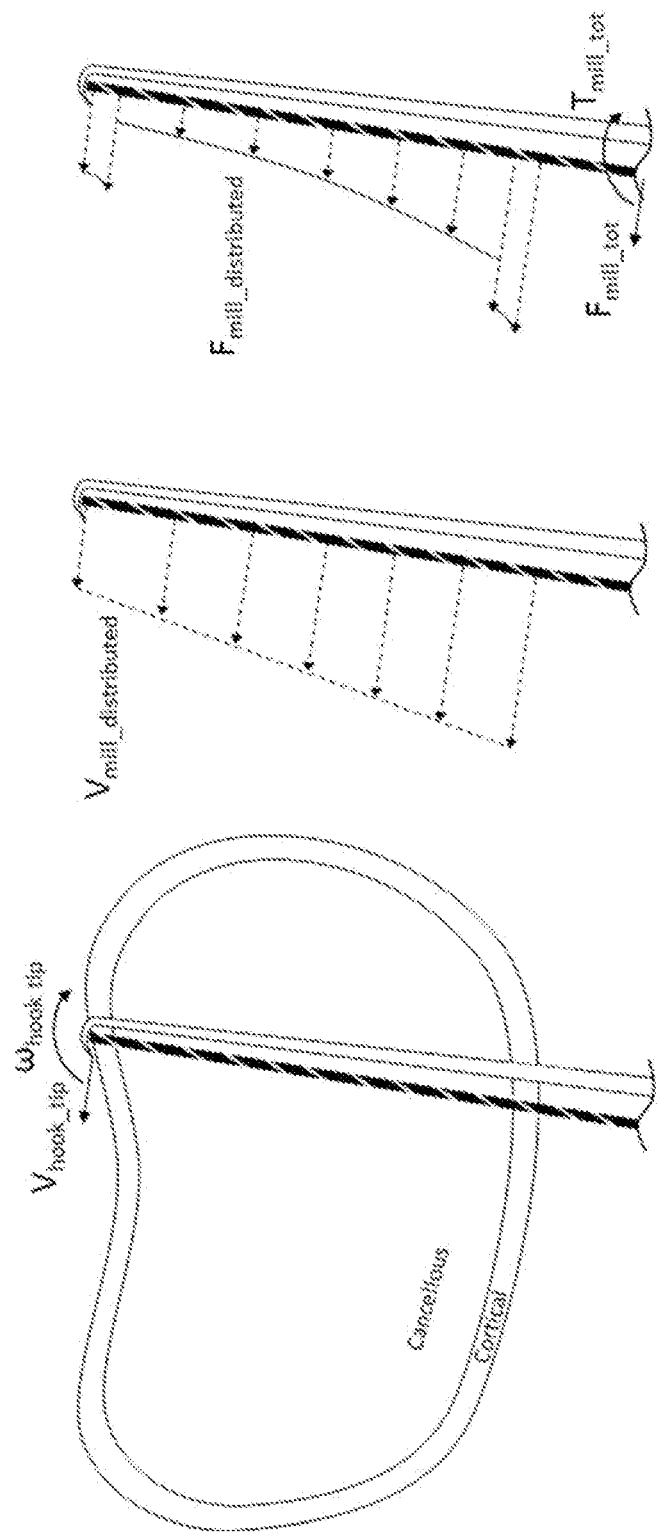
FIG. 21 illustrates a number of parameters used in an optimization algorithm of the milling speed used by a bone cutting system according to an embodiment of the present invention.

Sensor Feedback to Determine the Cutting Force of the Elongated Cutting Tool on the Bone To calculate the cutting speed, a predictive model that can be updated adaptively is used as will be further explained by FIG. 21. The model calculates the maximum allowable cutting speed in accordance with the maximum allowable cutting force and deflection of the cutter. The maximum allowable force is defined by the cutting device itself and by the maximum force that is allowed to be exerted on the bone without destabilizing the bone. The model may use a density map of the bone based on the CT-image data or a simplified model based on the structure of the bone namely cancellous or cortical bone. Both structures have a different density and strength, which results in a different cutting force. The information about the bone structure is combined with the local cutting speed to calculate the resulting cutting force. Based on a given linear speed of the hook tip ($v_{hook\_tip}$) and angular speed ($\omega_{hook\_tip}$), the distributed milling speed ($v_{mill\_distributed}$) is calculated. In combination with an empirical relationship between the cutting speed and cutting force, the distributed cutting force ($F_{mill\_distributed}$) is determined. From the distributed cutting force, the total milling force ($F_{mill\_total}$) and the total milling torque ($T_{mill\_tot}$) exerted by the cutter on the cutting motor assembly and the mill deflection are calculated. With an optimization algorithm the maximal linear and angular hook tip speed are calculated corresponding to the maximal milling force, torque and mill deflection.

The cutting force measured by a force sensor, for instance by sensor 511 as shown in FIG. 6, can be used to compensate for deviations on the prediction and to update the predictive model. All calculations are performed in real-time. This allows to obtain the fastest cutting time without exceeding the maximum allowable force and mill deflection. To limit the milling forces and deflection of the mill, the actual cutting length and mill load may be calculated in real-time. Depending on the moment, only a portion or the whole length of the mill may be used to cut the bone.

Separator Supporting Bone Cutting Tool

In some embodiments of the present invention, the second, typically non-driven, extremity of the milling cutter is in contact with the bent portion. The head of the milling cutter and the bent portion may include a supporting portion for receiving the second extremity of the elongated cutting tool. The supporting portion and the second extremity of the elongated cutting tool may for instance be engaging portions that fit each other. For example, the bent portion may include bearings, as explained in embodiments of the first aspect. Such a supporting portion may allow higher rigidity of the cutter 220, as there is less risk of bending the shaft 224. Thus, higher pressure and cutting speed can be attained. Alternatively or additionally, thinner milling cutters 220 can be used, which reduces the invasiveness of the cutting process.

Two-Step Cutting and One-Step Cutting.

In some embodiments of the present invention, the cutting portion of the bone cutting tool may extend along most of the length of the tool so that cutting occurs along substantially the full length of the tool. A milling cutter 230 having a cutting portion 233 extending along most of the length of the cutter is shown in FIG. 6. Typically, the full length of the mill that is provided with a cutting portion can be used for cutting. The non-cutting length of the mill does not interfere in the milling process and is irrelevant or the process. Typically, a non-cutting length is provided to introduce some distance between the incision area and the more bulky motor connection. This can be used for slot cutting, for example for providing slot cutting and slicing of a bone in a single step.

The difference between two-step cutting and single step cutting, for which the cutter 230 of FIG. 6 can be used, is explained in the following.

FIG. 4 shows a section view of the open bone, while FIG. 14 shows the bone with the upper part partly removed. For example, a portion of the bone not in contact with ligaments can be removed easily. Subsequently, parts of the bone can be cut out, for example parts with little or no ligament presence, e.g. by visual inspection or by mapping. While FIG. 14 shows that an upper part of the bone is removed, optionally, a slot 403 can be provided in the zone of the bone with less ligaments, by cutting with a mill without a protection element, for example with the arm removed, or with the arm 311 but without bent portion, so the top (or head end 221) of the milling cutter 220 is revealed and can be used for cutting, as shown in FIG. 5. Not removing the arm has the advantage that the arm can still provide cooling and/or aspiration, as well as support on the bone for guiding and reducing tilt of the blade. The parts of the bone wall most in contact with ligaments can be left with no cutting, leaving the hollow region 405 surrounded by a bone wall 401, also if slot cutting is provided.

At the end of the first step, a bone wall 401 is left untouched, including an external surface 402, as shown in FIG. 4. The second step comprises the more delicate operation of removing the bone wall 401. For the removal of the wall, a separator according to embodiments of the present invention can be used, thus protecting the ligaments present at the external surface 402. Hence, a rough, fast but partial removal of material leaving the bone wall 401 is followed by a careful removal of the wall using a separator, for example using a milling cutter 220 and a separator 121, as shown in FIGS. 3 and 4. This allows complete sectioning of the bone in a safe way in two steps.

The first step can be performed with a different bone cutting tool, or with the same bone cutting tool as in embodiments of the present invention but with the separator removed. When the separator is removed, it is possible to use the bone cutting tool for removing bone material from inside the bone, allowing using the bone cutting tool for rough preliminary cutting, which may reach up to a safe distance from the bone surface 402 that includes many ligaments. In some embodiments, the arm may remain without the bent portion. The arm can still be used to provide guiding through a slot, or to provide aspiration or cooling (e.g. cooling water) during the procedure. This is shown in FIG. 5. In other embodiments, both the arm and the bent portion can be removed. Perforating and drilling may also be possible, because the top portion of the bone cutting tool (e.g. the head end) can be revealed, for example using milling balls. Then the side walls left by the perforation can be removed, e.g. with a circular saw, as shown in FIG. 14

The present invention also allows complete sectioning of the bone in a single step, rather than two steps. Cutting control can advantageously be used for increasing regularity of cutting surfaces and/or speed.

Figure 10:
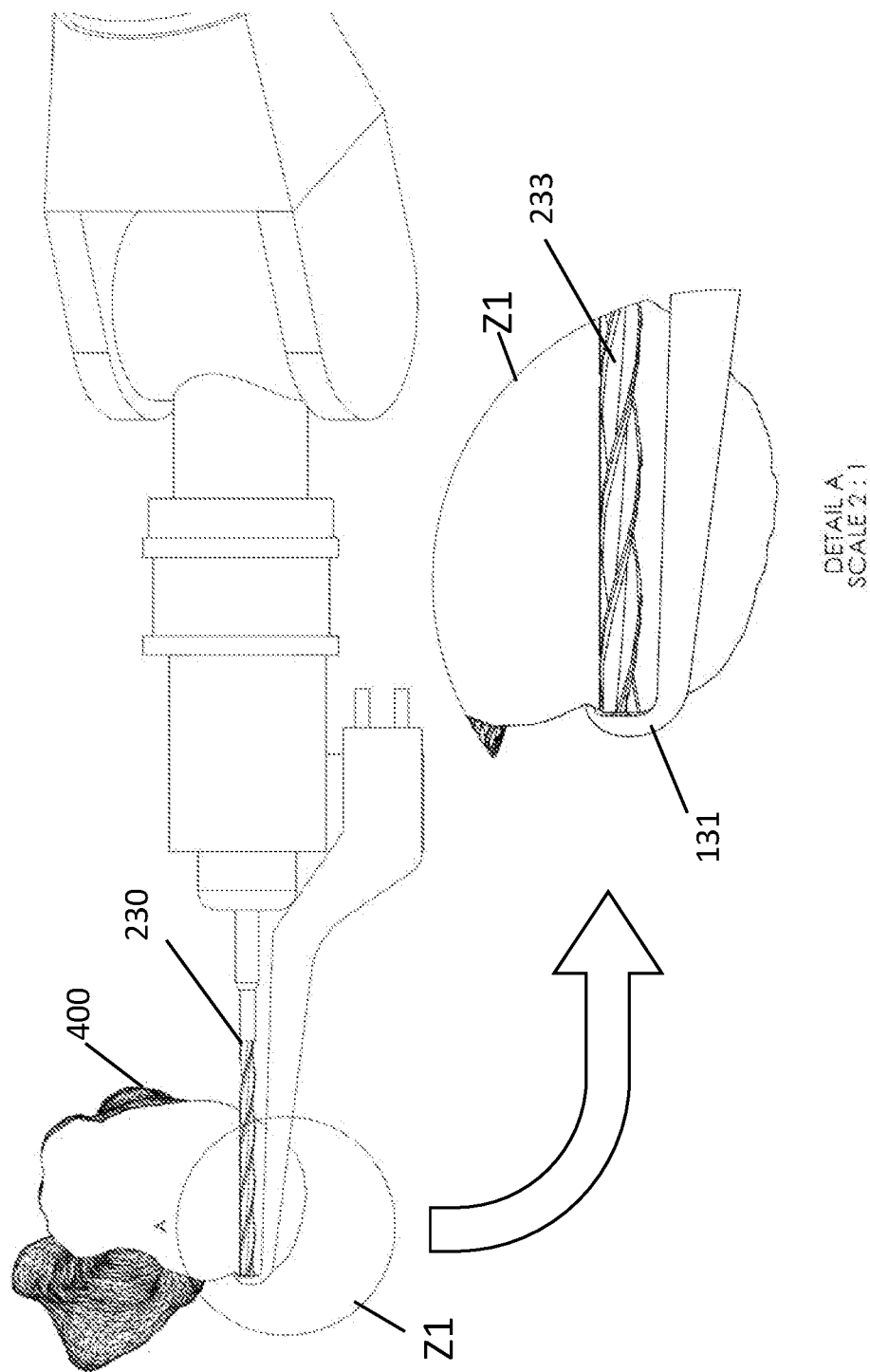
FIG. 10 illustrates a bone cutting tool including a protection system in accordance with embodiments of the present invention, and a detail of the cutting part, performing single-step cutting.

It is advantageous that the cutting portion 233 of a milling cutter 230 covers most of its length. This embodiment is shown in FIG. 6 and FIG. 10, and the zoomed portion Z of FIG. 10 shows the procedure. The bent portion 131 remains outside the bone, with its point resting on the surface and lifting any material such as ligaments, while it moves. The cutting portion 233 may have a length close to, or larger than, the average width of the bone that will be cut. The cutting may commence in a region where not a lot of ligaments are expected, with the bent portion facing the side of the bone with high density of ligaments and irregularities. It is to be noted that although, for a mil with a long cutting length, cutting can be done in a single step, also a two step process can be used whereby first the inside is cut without the protecting element, whereas in a second step, the remaining edge can be cut with the protecting element. When a mill is used with a short cutting length, such a two step process is always necessary.

Due to the strain at which the cutting portion 233 is submitted, if cutting the whole bone in a single step, it is preferred that in this embodiment the milling cutter 230 is supported by the bent portion 131, e.g. by bearings in the bent portion. This also improves rotation stability and allows the use of thin cutters. A bearing 154 is shown in FIG. 12. The bearing can be made of roller bearing, sliding bearing, hydrodynamic bearing, etc. Combinations of different bearing types is also possible. Metallic or plastic contact materials may be used. Lubrication may be used, such as for example but not limited to internally supplied water lubrication.

Figure 13:
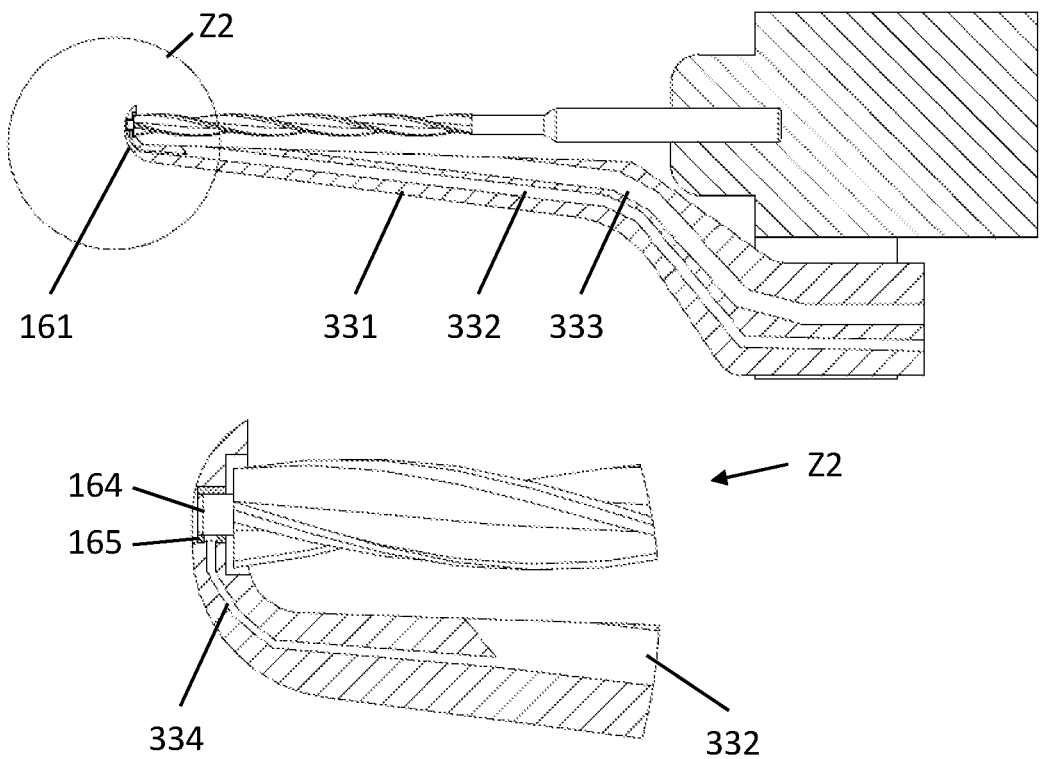
FIG. 13 illustrates a bone cutting tool including a protection system in accordance with an embodiment of the present invention.

FIG. 13 shows an exemplary embodiment of an arm 331 including internal conduits, for example water channels 332, 333. In this embodiment, the protection element 161 is a bent portion with a hydrodynamic bearing 164, shown in detail in the zoomed portion Z2, and the arm and bent portion includes an internal channel 334 for providing fluid (e.g. water) to the bearing system, e.g. to the bearing 164 and/or bearing bush 165. These provide good and stable bearing and allow high rotation speeds and/or longer rotation times, because temperature increase due to the movement of the milling cutter 230 is reduced both in the saw and in the bearing system.

The present invention can include means for automated cutting. FIG. 15 shows a setup with a robot arm 234 and a navigation system, for enabling automated cutting. This can be used with appropriate hardware and software, for example mapping software and data from patient scans or the like. A positioning or guiding system 601, 602 may be present in the bone 400 and on the robot arm 234 for controlling their relative position.

Figure 16:
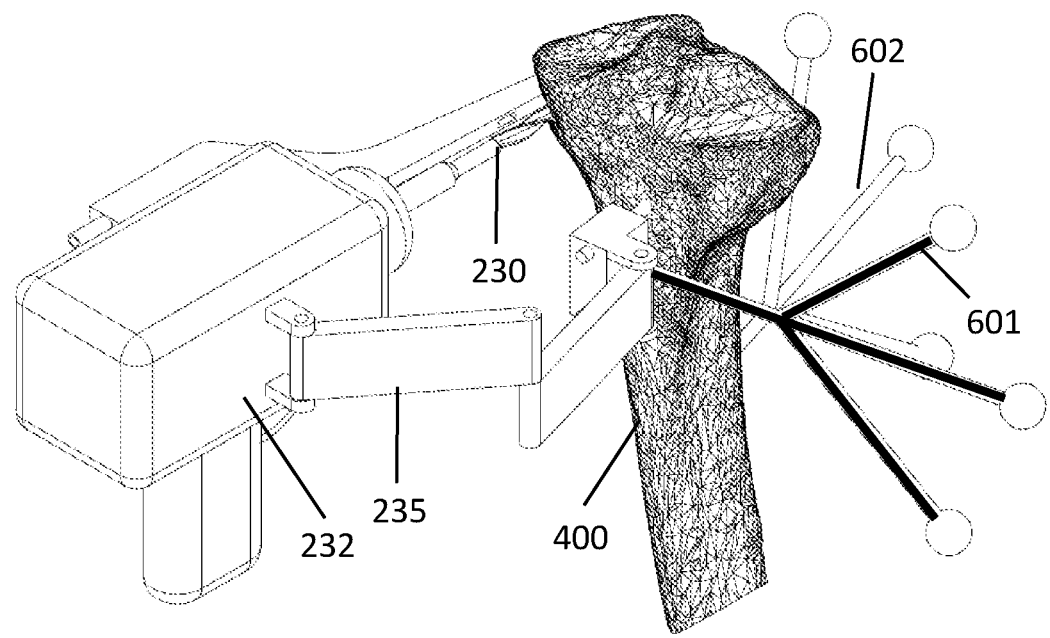
FIG. 16 and FIG. 17 illustrate two alternative bone cutting tools including a protection system, including means for providing manual cutting, in accordance with embodiments of the present invention.
Figure 17:
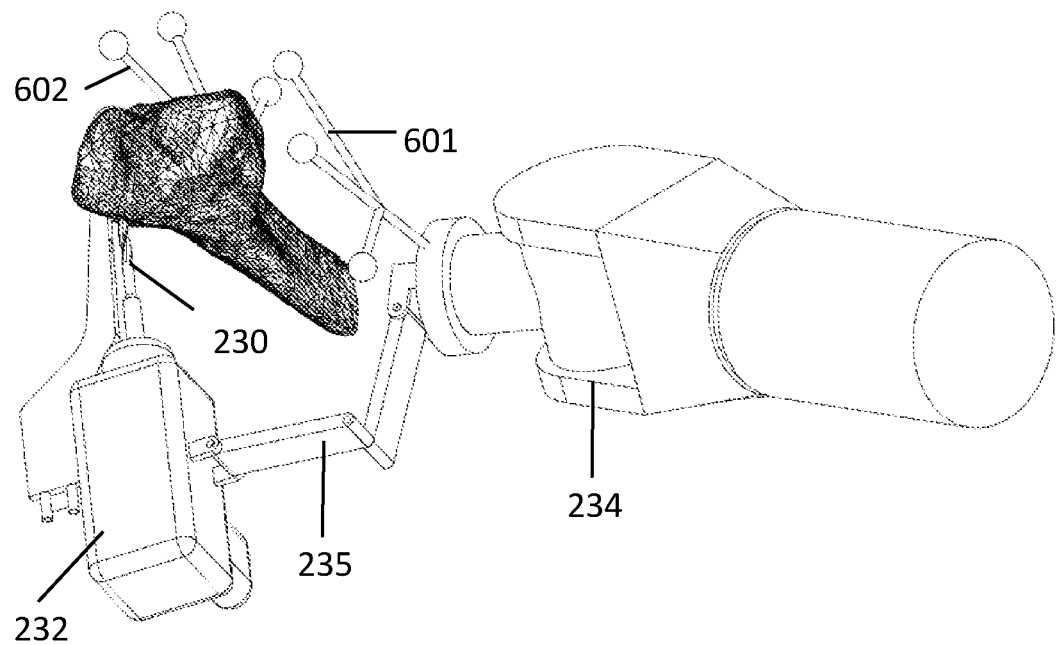

The present invention can alternatively include means for manual operation of the bone cutting system. FIG. 16 and FIG. 17 show a manually operated variant with tracking system 602 mounted on bone and a tracking system 602 mounted on cutting plane controlling support of the articulated extension mechanism. The cutter 230 is activated manually (e.g. by pressing a button or trigger, as in a drill) and moved also manually. For example, an articulated extension 235 may be attached to the frame 232, and it may restrict the movement of the drill to a plane (so the cutting path is restricted to a plane). The articulated extension 235 may be anchored (e.g. attached, tied, clamped, screwed, etc.) to the bone 400 as shown in FIG. 16, or alternatively to an external object, such as an arm, e.g. a robot arm 234 as shown in FIG. 17.

Although a milling cutter 230 as the embodiment of FIG. 6 is shown in FIG. 15, FIG. 16 and FIG. 17, any other cutting means can be used in combination with means for automated cutting (e.g. with the robot arm and navigation system) or with means for manual operation. Alternatively, semi-automated action may be performed, whereby there is a collaborative interaction between the operator and the system.

Overview of Protection Elements

Figure 18:
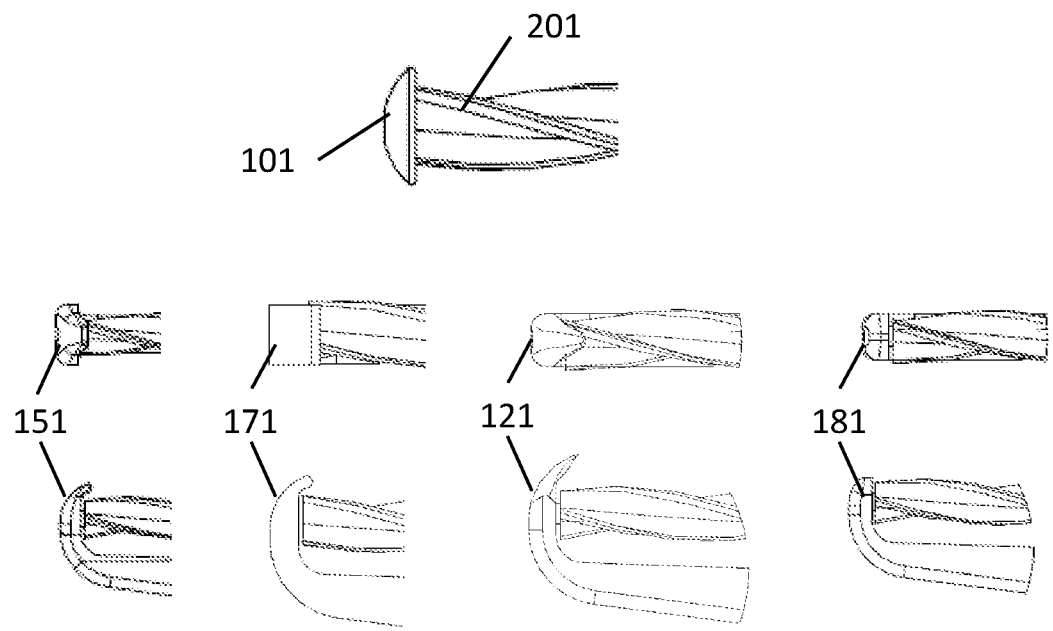
FIG. 18 illustrates several different protection elements in accordance with embodiments of the present invention.

FIG. 18 shows different protection elements. The protection element 101 of the uppermost drawing is a plate as explained with reference to FIG. 1. The lower two rows show the front and side views of four different embodiments. The first embodiment starting from the left shows a protection system comprising a bent portion 151 wider than the diameter of the mill as shown in FIG. 12. The second embodiment shows a protection system comprising a bent portion 171 with a soft, rounded tip, which does not scratch the surface of the bone, and only separates loose soft material from the surface. In this particular embodiment, no support bearing is provided. The third embodiment shows a protection system comprising a bent portion 121 with a sharp tip, for separating soft tissue from the bone surface, as explained with reference to embodiments shown in e.g. FIG. 4. The fourth embodiment shows a protection system comprising half bent portion 181, which does not shroud completely the cutting mill. Protection can still be provided by providing a suitable cutting direction and orientation, so the mill does not protrude from the cutting slot. Other features can be added or integrated to the protection element. For example, an electrocautery knife can be integrated in the edge to separate the soft tissue from the bone, or a high pressure waterjet can be used to remove the soft tissue from the bone. Also a mechanical movement can be imposed to the separator to improve the separation function.

Figure 19:
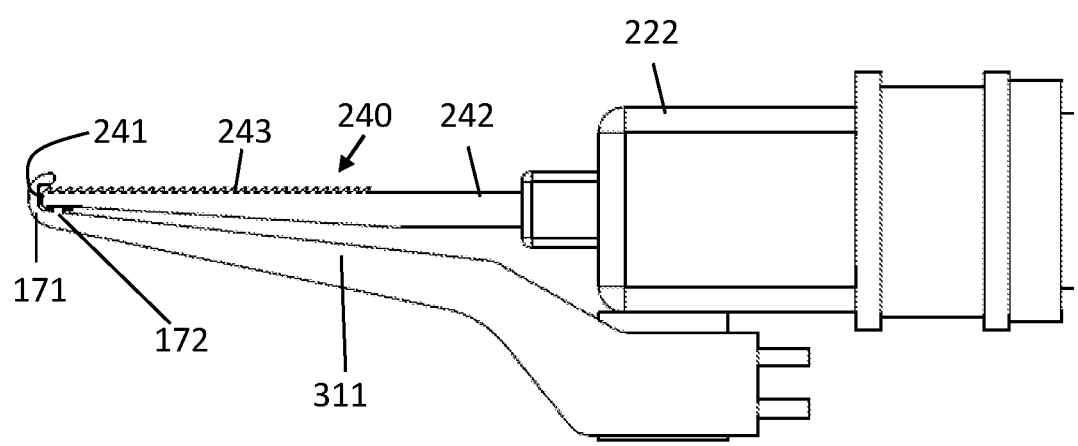
FIG. 19 illustrates a bone cutting tool according to an embodiment of the present invention.

Although the present disclosure deals mainly with milling cutters, other longitudinal cutting tools can be used, for example reciprocating saws as shown in FIG. 19. A miller cutter and a reciprocating saw 240 both usually comprise a longitudinal member with a proximal end 242 connected to the actuator 222, and a distal end opposite to the proximal end. The cutting portion 243 extends from the distal end or head end 241 towards the proximal end 242. The cutting portion 243 usually includes cutting areas in at least one side comprising serrated teeth, rather than helical grooves as in milling cutters. Also, while in milling cutters the head end may include cutting parts, in case of reciprocating saws the head end 241 is flat, but it may however damage by impact the soft tissue. In embodiments of the present invention, at least the head end 241 is covered or shrouded by the bent portion 171 of a protective element, so it does not touch soft tissue, while at least the cutting areas in the side perform the cutting. In this case, the bent portion 171 does not include a bearing, but the system may include a guide or support tab 172, on the bent portion or in the arm 311 supporting the sawblade, as shown in the figure.

It is to be noted that the bent portion 171 may cover a small part of the cutting portion 243, not only exclusively the head end 241. This is also the case of the milling cutter.

In summary, a bone cutting tool is provided which allows separation of ligaments from an area of the bone while cutting, before the bone cutting tool reached that area, by use of a separator that wedges between ligament and bone surface and moves together with the bone cutting tool. A sensor, for example a sensor for directly or indirectly measuring forces on the bone, may be used to determine the location of the edge of the bone. A sensor, for example a sensor for directly or indirectly measuring force on the elongated bone cutting tool may be used to determine the cutting force of the cutter on the bone. The determined cutting force may be used to adjust the cutting speed to obtain a maximal cutting speed while not exceeding the maximum allowable cutting force on the elongated cutting to avoid or limit stress on the elongated cutting tool or break the elongated cutting tool, to limit the forces on the bone, to avoid or limit bending of the elongated cutting tool so as to obtain a flat cut.

By way of illustration, embodiments of the present invention not being limited thereto, an example of an experiment of bone cutting is further discussed. In the experiment, the bone cutting tool was based on a mill with long cutting length and rather small diameter, whereby the bone cutting tool was further combined with a protection element according to an embodiment of the present invention. This allows to overcome the problem of having a slow cutting process due to the fact that different steps need to be applied in view of small cutting lengths. An appropriate selection of parameters also has resulted in a good thermal behavior, which is important in view of medical reasons. The use of a bone cutting tool according to an embodiment of the present invention also resulted in a decreased thermal necrosis for the surface of the remaining bone, which improves the natural ingrowth of cementless implants and reduces the risk of loosening of the implant.

It is an advantage of embodiments of the present invention that use can be made of a long mill, with a supported second extremity, i.e. supported through a bearing. Such a system reduces the risk of cutting soft tissue. A large cutting length, e.g. at least 45 mm, (but possibly more e.g. for the case of total knee replacement) enables to perform a cut in a single cutting action, resulting in a faster intervention. The small diameter of the mill, e.g. between 2 mm and 5 mm, e.g. about 4 mm, allows for slot cutting instead of milling all material away, resulting in a less invasive technique. The latter results in a lower risk of damaging other structures and an in lower forces that need to be used.

The minimal mill diameter can only be exploited by providing good support for the cutting portion of the cutting tool, thereby avoiding bending and breaking of the tool. This is supported by providing at the driven extremity a larger diameter and/or providing a bearing support at the second extremity, e.g. integrated in the protection system or protection element as described above. It is an advantage of embodiments of the present invention that a reduction of the diameter at the cutting portion can be obtained compared to existing systems.

Using the above embodiments, slot cutting in a single step in a minimal invasive way can be obtained.

In the experiment, it was clear that a selection of good mill geometry and operational cutting parameters is essential to good results with this milling cutter. If chosen well, the detrimental thermal necrosis impact can be reduced by a factor 4 compared to the conventional technique. This is highly beneficial to avoid implant loosening and to enable ingrowth with cementless implants. Also the flatness and accuracy of the cut is highly improved compared to the conventional technique as a result of these optimal milling parameters. Furthermore this also leads to lower cutting forces compared to conventional techniques, reducing thus errors as a result of bone motion during the cutting action. In a further aspect, the present invention also relates to a bone cutting system for cutting a bone of a subject for surgery. The bone cutting system according this aspect comprises an elongated surgical bone cutting tool adapted for cutting the bone. The elongated surgical bone cutting tool has a first extremity for fixing the elongated surgical bone cutting tool to a cutting robot or machinery and a second extremity opposite thereto at an end of the elongated surgical bone cutting tool. The bone cutting system further comprises a protection system comprising a protection element attachable to the elongated bone cutting tool or a frame of the elongated bone cutting tool.

The protection element includes an interposing portion covering, when the protection element is attached to the elongated bone cutting tool or the support of the elongated bone cutting tool, at least part of the second extremity of the elongated bone cutting tool, so that the interposing portion is being interposed between soft tissue surrounding the bone and the bone cutting tool during cutting with the elongated cutting tool, for preventing the bone cutting tool from cutting into soft tissue surrounding the bone.

According to embodiments of the present invention, the protection element further comprises a supporting portion for receiving and supporting at least a part of the second extremity of the elongated bone cutting tool. Such supporting typically may be obtained through a contact, e.g. direct contact, between the supporting portion and the second extremity to the elongated bone cutting tool.

Although embodiments are not being limited thereto, embodiments of the present aspect especially advantageously can be used with long and thin elongated bone cutting tools, e.g. elongated bone cutting tools allowing the cutting to be performed in a single cutting movement. A long cutting length, e.g. at least 45 mm, (but possibly more e.g. for the case of total knee replacement) thus enables to perform a cut in a single cutting action, resulting in a faster intervention. Advantageously, such a long cutting length is combined with a small diameter of the mill, e.g. between 2 mm and 5 mm, e.g. about 4 mm, allowing for slot cutting instead of milling all material away, resulting in a less invasive technique. The latter results in a lower risk of damaging other structures and an in lower forces that need to be used. Such a long length or minimal mill diameter can only be exploited by providing good support for the cutting portion of the cutting tool, thereby avoiding bending and breaking of the tool. The supporting portion may be a bearing support at the second extremity. Using the above embodiments, slot cutting in a single step in a minimal invasive way can be obtained. It is to be noted that other features of embodiments of the present aspect may be as described in the first aspect, but whereby the at least one sensor for extracting a contact force of the protection element on the bone is optional. Examples of embodiments of the present invention are illustrated in the drawings FIG. 1 to FIG. 19, whereby it will be understood that the at least one sensor for extracting a contact force of the protection element, when shown, is optional.

The invention claimed is:

1. A bone cutting system for cutting a bone of a subject, the bone cutting system comprising a surgical bone cutting tool adapted for cutting the bone, the surgical bone cutting tool having a first extremity for fixing the surgical bone cutting tool to a cutting robot or machinery and a second extremity opposite thereto at an end of the surgical bone cutting tool, the bone cutting system further comprising a protection system, the protection system comprising a protection element attachable to the bone cutting tool or to a frame of the bone cutting tool, wherein the protection element includes an interposing portion covering at least part of the second extremity of the bone cutting tool when the protection element is attached to the bone cutting tool or to the frame of the bone cutting tool, the interposing portion comprising an edge or point for separating the bone from soft tissue surrounding the bone and preventing the bone cutting tool from cutting into the soft tissue, so that the interposing portion is interposed between the soft tissue surrounding the bone and the bone cutting tool during cutting, and wherein during cutting with the cutting tool, the protection element follows in congruence with the bone cutting tool and wherein the bone cutting system comprises at least one sensor for extracting a contact force of the protection element on the bone, wherein the at least one sensor comprises a sensor which is provided on the surgical bone cutting tool or the frame of the surgical bone cutting tool for sensing a combined force including a cutting force of the bone cutting tool and the contact force of the protection element on the bone.

2. The bone cutting system of claim 1, wherein the at least one sensor comprises a sensor provided on or integrated in the protection element for sensing the contact force of the protection element on the bone.

3. The bone cutting system of claim 1, wherein the system is adapted for deriving a contact force of the protection element on the bone based on the sensing of an interaction between the surgical bone cutting tool and the bone.

4. The bone cutting system of claim 1, wherein the interposing portion is a bent portion for covering at least part of the second extremity of the cutting tool.

5. The bone cutting system of claim 1, wherein the protection system further includes an arm for holding the protection element, the arm being attachable to the bone cutting tool or the bone cutting tool frame of the cutting robot or machinery and the arm being positioned for following alongside the bone cutting tool during cutting with the bone cutting tool.

6. The bone cutting system of claim 1, wherein the interposing portion comprises a soft tissue separator for separating the soft tissue from the bone.

7. The bone cutting system of claim 6, wherein the soft tissue separator is any of a sharp edge, a blunt end, a sharp circular shape, a mechanically moving cutting device, a mechanically vibrating edge, an electrocautery knife or a pressure fluid jet.

8. The bone cutting system of claim 1, wherein the protection system includes a cooling system or an aspirator system for removing debris.

9. The bone cutting system of claim 1, wherein the protection element comprises a supporting portion for receiving and supporting at least a part of the second extremity of the bone cutting tool.

10. The bone cutting system of claim 9, wherein the supporting portion includes a bearing for supporting the second extremity of the bone cutting tool.

11. The bone cutting system of claim 1, wherein at least part of the protection element has a width larger than a width of the bone cutting tool.

12. Bone cutting system of claim 1, wherein the interposing portion is a bent portion that bends over the second extremity of the bone cutting tool covering at least part of a side surface of the bone cutting tool.

13. The bone cutting system of claim 1 further including a robot and a navigation system for locating the bone and the cutting tool in space.

14. The bone cutting system according to claim 13, wherein the bone cutting system comprises a controller for performing the cut automated based on information from the navigation system, a bone geometry and the sensor.

15. The bone cutting system of claim 1, wherein the bone cutting system is adapted for performing the cut manually, further including a mechanical guiding system connected to the bone, or to an external support for guiding the system along predetermined directions.

16. The bone cutting system according to claim 1, wherein the surgical bone cutting tool is elongated.

17. The bone cutting system according to claim 1, wherein the interposing portion is interposed between soft tissue surrounding the bone and the bone cutting tool during cutting with the cutting tool, for preventing the bone cutting tool from cutting into soft tissue surrounding the bone.

18. The bone cutting system according to claim 1, wherein the interposing portion is configured and dimensioned to be interposed between soft tissue surrounding the bone and the bone cutting tool during cutting with the cutting tool for preventing the bone cutting tool from cutting into soft tissue surrounding the bone.

19. The bone cutting system according to claim 1, wherein the interposing portion is hook shaped.

20. A bone cutting system for cutting a bone of a subject, the bone cutting system comprising a surgical bone cutting tool adapted for cutting the bone, the surgical bone cutting tool having a first extremity for fixing the surgical bone cutting tool to a cutting robot or machinery and a second extremity opposite thereto at an end of the surgical bone cutting tool, the bone cutting system further comprising a protection system, the protection system comprising a protection element attachable to the bone cutting tool or to a frame of the bone cutting tool,
wherein the protection element includes an interposing portion covering at least part of the second extremity of the bone cutting tool when the protection element is attached to the bone cutting tool or to the frame of the bone cutting tool, the interposing portion comprising an edge or point for separating the bone from soft tissue surrounding the bone and preventing the bone cutting tool from cutting into the soft tissue, so that the interposing portion is interposed between the soft tissue surrounding the bone and the bone cutting tool during cutting,
wherein during cutting with the cutting tool, the protection element follows in congruence with the bone cutting tool and wherein the bone cutting system comprises at least one sensor for extracting a contact force of the protection element on the bone,
wherein the protection element comprises a supporting portion for receiving and supporting at least a part of the second extremity of the bone cutting tool, and
wherein the supporting portion includes a separate and distinct bearing component for supporting the second extremity of the bone cutting tool.

* * * * *